(12) United States Patent
Doyle et al.

(10) Patent No.: US 7,846,439 B2
(45) Date of Patent: Dec. 7, 2010

(54) DOMAIN ANTIBODY CONSTRUCT

(75) Inventors: Anthony G. Doyle, Drummoyne (AU);
Benjamin P. Woolven, Cambridge (GB);
Ian M. Tomlinson, Cambridge (GB);
Jennifer A. Lee, Cambridge (GB);
Philip A. Jennings, Warrawee (AU)

(73) Assignee: Cephalon Australia Pty Ltd, Macquarie Park, NSW (AU)

( * ) Notice: Subject to any disclaimer, the term of this patent is extended or adjusted under 35 U.S.C. 154(b) by 390 days.

(21) Appl. No.: 11/670,261

(22) Filed: Feb. 1, 2007

(65) Prior Publication Data

US 2007/0202105 A1    Aug. 30, 2007

Related U.S. Application Data

(60) Provisional application No. 60/817,507, filed on Jun. 28, 2006.

(30) Foreign Application Priority Data

Feb. 1, 2006    (AU) ............... 2006900456

(51) Int. Cl.
*A61K 39/395*    (2006.01)
(52) U.S. Cl. .............. 424/135.1; 424/145.1; 530/387.3; 530/388.23
(58) Field of Classification Search ........................ None
See application file for complete search history.

(56) References Cited

U.S. PATENT DOCUMENTS

| | | | |
|---|---|---|---|
| 4,002,531 A | 1/1977 | Royer | |
| 4,816,567 A | 3/1989 | Cabilly et al. | |
| 5,223,409 A | 6/1993 | Ladner et al. | |
| 5,225,539 A | 7/1993 | Winter | |
| 5,349,052 A | 9/1994 | Delgado et al. | |
| 5,403,484 A | 4/1995 | Ladner et al. | |
| 5,427,908 A | 6/1995 | Dower et al. | |
| 5,571,698 A | 11/1996 | Ladner et al. | |
| 5,580,717 A | 12/1996 | Dower et al. | |
| 5,585,089 A | 12/1996 | Queen et al. | |
| 5,612,460 A | 3/1997 | Zalipsky | |
| 5,627,052 A | 5/1997 | Schrader | |
| 5,837,500 A | 11/1998 | Ladner et al. | |
| 5,885,793 A | 3/1999 | Griffiths et al. | |
| 5,892,019 A | 4/1999 | Schlom et al. | |
| 5,969,108 A | 10/1999 | McCafferty et al. | |
| 5,977,307 A | 11/1999 | Friden et al. | |
| 5,994,510 A | 11/1999 | Adair et al. | |
| 6,821,505 B2 | 11/2004 | Ward | |
| 2003/0039649 A1 | 2/2003 | Foote | |
| 2003/0118592 A1* | 6/2003 | Ledbetter et al. ......... 424/178.1 | |
| 2003/0143682 A1 | 7/2003 | Nicolaides et al. | |
| 2003/0199679 A1 | 10/2003 | Adair et al. | |
| 2003/0215427 A1 | 11/2003 | Jensen | |
| 2003/0232971 A1 | 12/2003 | Rathjen et al. | |
| 2004/0101905 A1 | 5/2004 | Brekke et al. | |
| 2004/0132101 A1 | 7/2004 | Lazar et al. | |
| 2005/0118643 A1 | 6/2005 | Burgess et al. | |
| 2005/0226863 A1 | 10/2005 | Colby et al. | |
| 2005/0271663 A1 | 12/2005 | Ignatovich et al. | |
| 2006/0024308 A1 | 2/2006 | Crea et al. | |
| 2006/0034845 A1 | 2/2006 | Silence et al. | |
| 2006/0038027 A1 | 2/2006 | O'Conner et al. | |
| 2006/0073141 A1 | 4/2006 | Ignatovich et al. | |
| 2006/0083747 A1 | 4/2006 | Winter et al. | |
| 2006/0210526 A1 | 9/2006 | Brocchini et al. | |
| 2007/0003549 A1 | 1/2007 | Ignatovich et al. | |
| 2007/0111281 A1 | 5/2007 | Sondermann et al. | |
| 2007/0269449 A1 | 11/2007 | Walczak | |
| 2008/0071063 A1 | 3/2008 | Allan et al. | |
| 2008/0095767 A1 | 4/2008 | Jennings et al. | |
| 2008/0139790 A1 | 6/2008 | Jennings et al. | |
| 2008/0227958 A1 | 9/2008 | Thompson et al. | |
| 2008/0241166 A1 | 10/2008 | Tomlinson et al. | |
| 2008/0255343 A1 | 10/2008 | Jennings et al. | |
| 2008/0260738 A1 | 10/2008 | Moore et al. | |
| 2009/0075338 A1 | 3/2009 | Moore et al. | |
| 2009/0081233 A1 | 3/2009 | Ignatovich et al. | |
| 2009/0148905 A1 | 6/2009 | Ashman et al. | |
| 2009/0221803 A1 | 9/2009 | Dall'Acqua et al. | |
| 2009/0226428 A1 | 9/2009 | Woolven et al. | |
| 2009/0258012 A1 | 10/2009 | Ignatovich et al. | |

(Continued)

FOREIGN PATENT DOCUMENTS

EP    0 368 684 B2    5/1990

(Continued)

OTHER PUBLICATIONS

Schneider et al., Proc Natl Acad Sci U S A. Apr. 1988;85(8):2509-13.*

(Continued)

*Primary Examiner*—Zachary Skelding

(57) ABSTRACT

The present invention provides a domain antibody construct which binds to human TNF-α, with the construct comprising:
(a) a domain antibody (dAb) which binds to human TNF-α;
(b) a modified hinge region sequence;
(c) a human or primate heavy chain constant region sequence having a truncated $C_H1$ domain of not more than 20 residues, wherein the modified hinge region sequence contains either a deletion or a single amino acid substitution of at least one cysteine residue which normally facilitates disulfide bond formation between heavy and light antibody chains.

4 Claims, 18 Drawing Sheets

U.S. PATENT DOCUMENTS

2009/0286962 A1 11/2009 Woolven et al.

FOREIGN PATENT DOCUMENTS

| EP | 0 436 597 B1 | 7/1991 |
| EP | 0 527 839 B1 | 2/1993 |
| EP | 0 589 877 B2 | 4/1994 |
| EP | 0 605 442 B1 | 7/1994 |
| WO | WO 88/01649 | 3/1988 |
| WO | WO-89/01974 A1 | 3/1989 |
| WO | WO-89/07142 A1 | 8/1989 |
| WO | WO-91/17271 A1 | 11/1991 |
| WO | WO-92/02551 A1 | 2/1992 |
| WO | WO-92/09690 A2 | 6/1992 |
| WO | WO-92/09690 A3 | 6/1992 |
| WO | WO-92/20791 A1 | 11/1992 |
| WO | WO-93/02108 A1 | 2/1993 |
| WO | WO-95/06058 A1 | 3/1995 |
| WO | WO-97/08320 A1 | 3/1997 |
| WO | WO-97/29131 A1 | 8/1997 |
| WO | WO 97/34631 | 9/1997 |
| WO | WO-98/31700 A1 | 7/1998 |
| WO | WO-98/32466 A1 | 7/1998 |
| WO | WO-98/49286 A3 | 11/1998 |
| WO | WO-99/26711 A1 | 6/1999 |
| WO | WO-99/36569 A1 | 7/1999 |
| WO | WO-00/40712 A1 | 7/2000 |
| WO | WO 00/042072 | 7/2000 |
| WO | WO-02/077029 A2 | 10/2002 |
| WO | WO-02/077029 A3 | 10/2002 |
| WO | WO-03/085089 A2 | 10/2003 |
| WO | WO-03/085089 A3 | 10/2003 |
| WO | WO-2004/003019 A2 | 1/2004 |
| WO | WO-2004/003019 A3 | 1/2004 |
| WO | WO 2004/058820 | 7/2004 |
| WO | WO 2004/058821 | 7/2004 |
| WO | WO 2004/058822 | 7/2004 |
| WO | WO 2004058820 A2 * | 7/2004 |
| WO | WO-2004/081026 A2 | 9/2004 |
| WO | WO-2004-081026 A3 | 9/2004 |
| WO | WO-2005/003345 A2 | 1/2005 |
| WO | WO-2005/003345 A3 | 1/2005 |
| WO | WO-2005/035572 A2 | 4/2005 |
| WO | WO-2005/035572 A3 | 4/2005 |
| WO | WO-2005/047325 A2 | 5/2005 |
| WO | WO-2005/047325 A3 | 5/2005 |
| WO | WO 2005/063816 | 7/2005 |
| WO | WO-2006/003388 A2 | 1/2006 |
| WO | WO-2006/003388 A3 | 1/2006 |
| WO | WO-2006/096653 A2 | 9/2006 |
| WO | WO-2007/019620 A1 | 2/2007 |
| WO | WO-2007/019621 A1 | 2/2007 |
| WO | WO-2007/070948 A1 | 6/2007 |
| WO | WO-2007/070979 A1 | 6/2007 |
| WO | WO-2007/087673 A1 | 8/2007 |
| WO | WO 2009/006520 | 1/2009 |
| WO | WO 2009/134776 | 11/2009 |
| WO | WO 2009/143472 | 11/2009 |

OTHER PUBLICATIONS

Brekke et al., Immunol Today. Feb. 1995;16(2):85-90.*
Saerens et al., J Mol Biol. Sep. 23, 2005;352(3):597-607.*
Rudikoff et al., Proc. Natl. Acad. Sci. USA, 79: 1979-1983, Mar. 1982.*
International Search Report mailed on Mar. 26, 2007, for PCT Application No. PCT/AU2006/001993 filed on Dec. 20, 2006, three pages.
Qi, Y. et al. (1995). "A Genetically Engineered Single-Gene-Encoded Anti-TAG72 Chimeric Antibody Secreted From Myeloma Cells," Hum. Antibodies Hybridomas 6(4):161-166 (Abstract only located at PubMed last visited Feb. 26, 2007, one page).
Davies, J. et al. (1996). "Affinity Improvement of Single Antibody VH Domains: Residues in all Three Hypervariable Regions Affect Antigen Binding," Immunotechnology 2:169-179.
Foote, J. et al. (1992). "Antibody Framework Residues Affecting the Conformation of the Hypervariable Loops," J. Mol. Biol. 224:487-499.
Hwang, W.Y.K. et al. (2005). "Use of Human Germline Genes in a CDR Homolgy-Based Approach to Antibody Humanization," Methods 36:35-42.
Jones, P.T. et al. (May 29, 1986). "Replacing the Complementarity-Determining Regions in a Human Antibody with those from a Mouse," Nature 321:522-525.
Reiter, Y. et al. (1999). "An Antibody Single-Domain Phage Display Library of a Native Heavy Chain Variable Region: Isolation of Functional Single-Domain VH Molecules with a Unique Interface," J. Mol. Biol. 290:685-698.
Sidhu, S.S. et al. (2004). "Phage-Displayed Antibody Libraries of Synthetic Heavy Chain Complementarity Determining Regions," J. Mol. Biol. 338:299-310.
Speidel, M.T. et al. (1989). "Detection of Human and Marmoset Immunoglobulin Heavy Chain by a Polyclonal Antiserum to a Marmoset Immunoglobulin-Related T Cell Product," Expl. Clin. Immuno. 6:245-250.
Supplementary European Search Report mailed Jun. 18, 2009, for EP Application No. 06774812.9, 10 pages.
Supplementary European Search Report mailed Jun. 18, 2009, for EP Application No. 06774813.7, eight pages.
Supplementary European Search Report mailed Jun. 18, 2009, for EP Application No. 06828046.0, nine pages.
Supplementary European Search Report mailed Jun. 18, 2009, for EP Application No. 06840403.7, 10 pages.
Babcook, J.S. et al. (Jul. 1996). "A Novel Strategy for Generating Monoclonal Antibodies from Single, Isolated Lymphocytes Producing Antibodies of Defined Specificities," Proc. Natl. Acad. Sci. USA 93:7843-7848.
Barbas III, C.F. et al. (Sep. 1991). "Assembly of Combinatorial Antibody Libraries on Phage Surfaces: The Gene III Site," Proc. Natl. Acad. Sci. USA 88:7978-7982.
Bird, R.E. et al. (Oct. 21, 1988). "Single-Chain Antigen-Binding Proteins," Science 242:423-426.
Chirino, A.J. (Jan. 2004). "Minimizing the Immunogenicity of Protein Therapeutics," Drug Discovery Today 9(2):82-90.
Clackson, T. et al. (Aug. 15, 1991). "Making Antibody Fragments Using Phage Display Libraries," Nature 352:624:628.
Conrad, U. et al. (1998). "Compartment-Specific Accumulation of Recombinant Immunoglobulins in Plant cells: An Essential Tool for Antibody Production and Immunomodulation of Physiological Functions and Pathogen Activity," Plant Molecular Biology 38:101-109.
Cramer, C.L. et al. (1999). "Transgenic Plants for Therapeutic Proteins: Linking Upstream and Downstream Strategies," Chapter 240 In Current Topics in Microbiology and Immunology, R.W. Compans et al. eds., Springer-Verlag: Berlin, pp. 95-118.
Delgado, C. et al. (1992). "The Uses and Properties of PEG-Linked Proteins," Critical Reviews in Therapeutic Drug Carrier Systems 9(3,4):249-304.
Devereux, J. et al. (1984). "A Comprehensive Set of Sequence Analysis Programs for the VAX," Nucleic Acids Research 12(1):387-395.
Ehrlich, P.H. et al. (1987). "Rhesis Monkey Responses to Multiple Injections of Human Monoclonal Antibodies," Hybridoma 6(2):151-160.
Ehrlich, P.H. et al. (1988). "Human and Primate Monoclonal Antibodies for in Vivo Therapy," Clinical Chemistry 34(9):1681-1688.
Fischer, R. et al. (1999). "Towards Molecular Farming in the Future: Moving from Diagnostic Protein and Antibody Production in Microbes to Plants," Biotechnol. Appl. Biochem. 30:101-108.
Francis, G.E. et al. (1998). "PEGylation of Cytokines and Other Therapeutic Proteins and Peptides: The Importance of Biological Optimisation of Coupling Techniques," International Journal of Hematology 68:1-18.
Fuchs, P. et al. (Dec. 1991). "Targeting Recombinant Antibodies to the Surface of Escherichia coli: Fusion to a Peptidoglycan Associated Lipoprotein," Bio/Technology 9:1369-1372.

Garrard, L.J. et al. (Dec. 1991). "F$_{AB}$ Assembly and Enrichment in a Monovalent Phage Display System," *Bio/Technology* 9:1373:1377.

GenBank Accession No. AAB37424, created Dec. 13, 2006, located at http://www.ncbi.nlm.nih.gov/entrez/viewer.fcgi?db=protein&id=9665263, last visited on Aug. 8, 2007, 3 pages.

Gram, H. et al. (Apr. 1992). "In Vitro Selection and Affinity Maturation of Antibodies from a Naive Combinatorial Immunoglobulin Library," *Proc. Natl. Acad. Sci. USA* 89:3576-3580.

Griffiths, A.D. et al. (1993). "Human Anti-Self Antibodies with High Specificity from Phage Display Libraries," *The EMBO Journal* 12(2):725-734.

Hammer, J. et al. (Dec. 1994). "Precise Prediction of Major Histocompatibility Complex Class II-Peptide Interaction Based on Peptide Side Chain Scanning," *J. Exp. Med.* 180:2353-2358.

Hawkins, R.E. et al. (1992). "Selection of Phage Antibodies by Binding Affinity Mimicking Affinity Maturation," *J. Mol. Biol.* 226:889-896.

Hay, B.N. et al. (Apr. 1992). "Bacteriophage Cloning and *Escherichia coli* Expression of a Human IgM Fab," *Hum. Antibod. Hybridomas* 3:81-85.

Holliger, P. et al. (Jul. 1993). "'Diabodies': Small Bivalent and Bispecific Antibody Fragments," *Proc. Natl. Acad. Sci. USA* 90:6444-6448.

Holt, L.J. et al. (Nov. 2003). "Domain Antibodies: Proteins for Therapy," *TRENDS in Biotechnology* 21(11):484-490.

Hood, E.E. et al. (1999). "Molecular Farming of Industrial Proteins from Transgenic Maize," *Adv. Exp. Med. Biol.* 464:127-147.

Hoogenboom, H.R. et al. (1991). "Multi-Subunit Proteins on the Surface of Filamentous Phage: Methodologies for Displaying Antibody (Fab) Heavy and Light Chains," *Nucleic Acids Research* 19(15):4133-4137.

Huse, W.D. et al. (Dec. 8, 1989). "Generation of a Large Combinatorial Library of the Immunoglobulin Repertoire in Phage Lambda," *Science* 246:1275-1281.

Huston, J.S. et al. (Aug. 1988). "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883.

International Search Report mailed on Oct. 30, 2006, for PCT Application No. PCT/AU2006/001165 filed on Aug. 15, 2006, one page.

International Search Report mailed on Oct. 30, 2006, for PCT Application No. PCT/AU2006/001166 filed on Aug. 15, 2006, one page.

International Search Report mailed on Mar. 15, 2007, for PCT Application No. PCT/AU2006/001940 filed on Dec. 20, 2007, three pages.

International Search Report mailed on Mar. 16, 2007, for PCT Application No. PCT/AU2007/000085 filed on Feb. 1, 2007, three pages.

Irving, R.A. et al. (2001). "Ribosome Display and Affinity Maturation: From Antibodies to Single V-Domains and Steps Towards Cancer Therapeutics," *Journal of Immunological Methods* 248:31-45.

Kabat E.A. et al. (1971). "Attempts to Locate Complementarity-Determining Residues in the Variable Positions of Light and Heavy Chains," *Annals New York Academy of Sciences* pp. 382-393.

Kabat, E.A. et al. (1983). "Sequences of Proteins of Immunological Interest, Tabulation and Analysis of Amino Acid and Nucleic Acid Sequences of Precursors, V-Regions, C-Regions, J-Chain, $\beta_2$-Microglobulins, Major Histocompatibility Antigens, Thy-1, Complement, C-Reactive Protein, Thymopoietin, Post-Gamma Globulin, and $\alpha_2$-Macroglobulin," *U.S. Department of Health and Human Services*, 349 pages.

Keffer, J. et al. (1991). "Transgenic Mice Expressing Human Tumour Necrosis Factor: A Predictive Genetic Model of Arthritis," *The EMBO Journal* 10(13):4025-4031.

Kipriyanov, S.M. et al. (1994). "Recombinant Single-Chain Fv Fragments Carrying C-Terminal Cysteine Residues: Production of Bivalent and Biotinylated Miniantibodies," *Mol. Immunol.* 31:1047-1058.

Kipriyanov, S.M. et al. (1995). "Single-Chain Antibody Streptavidin Fusions: Tetrameric Bifunctional scFv-Complexes with Biotin Binding Activity and Enhanced Affinity to Antigen," *Hum. Antibod. Hybridomas* 6(3):93-101.

Knappik, A. et al. (2000). "Fully Synthetic Human Combinatorial Antibody Libraries (HuCAL) Based on Modular Consensus Frameworks and CDRs Randomized with Trinucleotides," *J. Mol. Biol.* 296:57-86.

Kong, Y-Y. et al. (Jan. 28, 1999). "OPGL is a Key Regulator of Osteoclastogenesis, Lymphocyte Development and Lymph-Node Organogenesis," *Nature* 397:315-323.

Kong, Y-Y. et al. (Nov. 18, 1999). "Activated T Cells Regulate Bone Loss and Joint Destruction in Adjuvant Arthritis Through Osteoprotegerin Ligand," *Nature* 402:304-309.

Kozlowski, A. et al. (2001). "Improvements in Protein PEGylation: Pegylated Interferons for Treatment of Hepatitis C," *Journal of Controlled Release* 72:217-224.

Langermans, J.A.M. et al. (2000). "Reactivity of Human T-Lymphocyte-Specific Antibodies with Peripheral Blood Mononuclear Cells and Spleen of *Aotus azarae* ssp. *boliviensis* (Owl Monkey)," *J. Med. Primatol.* 29:397-401.

Ma, J.K.-C. et al. (1995). "Plant Antibodies for Immunotherapy," *Plant Physiol.* 109:341-346.

Ma, J.K.-C. et al. (Dec. 1995). "Immunotherapeutic Potential of Antibodies Produced in Plants," TIBECH 13, 6 pages.

Matthews, N. et al. (1987). "Cytotoxicity Assays for Tumour Necrosis Factor and Lymphotoxin" Chapter 12 *In Lymphokines and Interferons, a Practical Approach*, Clemens, M.J. et al., eds., IRL Press, pp. 221-225.

McCafferty, J. et al. (Dec. 6, 1990). "Phage Antibodies: Filamentous Phage Displaying Antibody Variable Domains," *Nature* 348:552-554.

Muñoz, E. et al. (1998). "The $C_H1$ Domain of IgG is Not Essential for C3 Covalent Binding: Importance of the Other Constant Domains as Targets for C3," *International Immunology* 10(2):97-106.

Needleman, S.B. et al. (1970). "A General Method Applicable to the Search for Similarities in the Amino Acid Sequence of Two Proteins," *J. Mol. Biol.* 48:443-453.

Oh, H. et al. (Aug. 1999). "The Potential Angiogenic Role of Macrophages in the Formation of Choroidial Neovascular Membranes," *Investigative Ophthalmology & Visual Science* 40(9):1891-1898.

Pankow, R. et al. (2000). "The HTLV-I Tax Protein Transcriptionally Modulates OX40 Antigen Expression," *The Journal of Immunology* 165:263-270.

Poljak, R.J. et al. (Dec. 15, 1994). "Production and Structure of Diabodies," *Structure* 2:1121-1123.

Qin, W. et al. (2007). "A Novel Domain Antibody Rationally Designed Against TNF-α Using Variable Region of Human Heavy Chain Antibody as Scaffolds to Display Antagonistic Peptides," *Molecular Immunology* 44:2355-2361.

Rajpal, A. et al. (Jun. 14, 2005). "A General Method for Greatly Improving the Affinity of Antibodies by Using Combinatorial Libraries," *Proc. Natl. Acad. Sci. USA* 102(24):8466-8471.

Roberts, R.W. et al. (Nov. 1997). "RNA-Peptide Fusions for the in vitro Selection of Peptides and Proteins," *Proc. Natl. Acad. Sci. USA* 94:12297-12302.

Scallon, B.J. et al. (Apr. 1995). "Chimeric Anti-TNF-α Monoclonal Anti-Body cA2 Binds Recombinant Transmembrane TNF-α and Activates Immune Effector Functions," *Cytokine* 7(3):251-259.

Stern, A.S. et al. (Sep. 1990). "Purification to Homogeneity and Partial Characterization of Cytotoxic Lymphocyte Maturation Factor from Human B-Lymphoblastoid Cells," *Proc. Natl. Acad. Sci. USA* 87:6808-6812.

U.S. Appl. No. 11/636,338, filed Dec. 8, 2006, for Jennings et al.
U.S. Appl. No. 11/659,009, filed Jan. 30, 2007, for Jennings et al.
U.S. Appl. No. 11/830,713, filed Jul. 30, 2007, for Woolven et al.
U.S. Appl. No. 11/831,731, filed Jul. 31, 2007, for Doyle et al.
U.S. Appl. No. 11/831,751, filed Jul. 31, 2007, for Jennings et al.
U.S. Appl. No. 11/832,553, filed Aug. 1, 2007 for Jennings et al.

Van den Beucken, T. et al. (2001). "Building Novel Binding Ligands to B7.1 and B7.2 Based on Human Antibody Single Variable Light Chain Domains," *J. Mol. Biol.* 310:591-601.

Von Büdingen, H-C. et al. (2001). "Characterization of the Expressed Immunoglobulin IGHV Repertoire in the New World Marmoset *Callithrix jacchus*," *Immunogenetics* 53:557-563.

Walter et al. (1996). "Sequences of the Human Germline $V_H$, $V_K$, $J_H$ and $J_K$ Segments," *In Antibody Engineering: A Practical Approach*, pp. 316-318.

Ward, E.S. et al. (Oct. 12, 1989). "Binding Activities of a Repertoire of Single Immunoglobulin Variable Domains Secreted from *Escherichia coli*," *Nature* 341:544-546.

Whitelam, G.C. et al. (1994). "Antibody Production in Transgenic Plants," *Biochem. Soc. Trans.* 22:940-944.

Demarest, S.J. et al. (Sep. 2008). "Antibody Therapeutics, Antibody Engineering, and the Merits of Protein Stability," *Curr. Opin. Drug Discov. Devel.* 11(5):675-687. (Abstract Only).

Martin, A.C.R. (2008). "The Kabat Numbering Scheme," located at <http://www.bioinf.org.uk/abs/>, last visited Mar. 9, 2008, eight pages.

Paz, K. et al. (Nov. 2005). "Human Single-Domain Neutralizing Intrabodies Directed Against Etk Kinase: A Novel Approach to Impair Cellular Transformation," *Mo. Cancer Ther.* 4(11):1801-1809.

Brorson, K. et al. (1999). "Mutational Analysis of Avidity and Fine Specificity of Anti-Levan Antibodies," *The Journal of Immunology* 163:6694-6701.

Brummell, D.A. et al. (Feb. 1993). "Probing the Combining Site of an Anti-Carbohydrate Antibody by Saturation-Mutagenesis: Role of the Heavy-Chain CDR3 Residues," *Biochemistry* 32:1180-1187 (Abstract from PubMed only).

Burks, E.A. et al. (Jan. 1997). "In Vitro Scanning Saturation Mutagenesis of an Antibody Binding Pocket," *Proc. Natl. Acad. Sci. USA* 94:412-417.

Casset, F. et al. (2003). "A Peptide Mimetic of an Anti-CD4 Monoclonal Antibody by Rational Design," *Biochemical and Biophysical Research Communications* 307:198-205.

Chen, Y. et al. (1999). "Selection and Analysis of an Optimized Anti-VEGF Antibody: Crystal Structure of an Affinity-Matured Fab in Complex with Antigen," *J. Mol. Biol.* 293:865-881.

Colman, P.M. (1994). "Effects of Amino Acid Sequence Changes on Antibody-Antigen Interactions," *Research in Immunol.* 145:33-36.

De Pascalis, R. et al. (2002). "Grafting of 'Abbreviated' Complementarity-Determining Regions Containing Specificity-Determining Residues Essential for Ligand Contact to Engineer a Less Immunogenic Humanized Monoclonal Antibody," *The Journal of Immunology* 169:3076-3084.

Dufner, P. et al. (2006, e-pub. Sep. 26, 2006). "Harnessing Phage and Ribosome Display for Antibody Optimisation," *Trends Biotechnol.* 24(11):523-529.

Holm, P. et al. (2007). "Functional Mapping and Single Chain Construction of the Anti-Cytokeratin 8 Monoclonal Antibody TS1," *Mol. Immunol.* 44:1075-1084.

Jang, Y.-J. et al. (1998). "The Structural Basis for DNA Binding by an Anti-DNA Autoantibody," *Mol. Immunol.* 35:1207-1217.

Kobayashi, H. et al. (1999). "Tryptophan H33 Plays an Important Role in Pyrimidine (6-4) Pyrimidone Photoproduct Binding by a High-Affinity Antibody," *Protein Engineering* 12(10):879-884.

Kumar, S. et al. (Nov. 10, 2000). "Molecular Cloning and Expression of the Fabs of Human Autoantibodies in *Escherichia coli*," *J. Biol. Chem.* 275(45):35129-35136.

MacCallum, R.M. et al. (1996). "Antibody-Antigen Interactions: Contact Analysis and Binding Site Topography," *J. Mol. Biol.* 262:732-745.

Non-Final Office Action mailed Oct. 29, 2008, for U.S. Appl. No. 11/636,338, filed Dec. 8, 2006, 25 pages.

Smith-Gill, S.J. et al. (Dec. 15, 1987). "Contributions of Immunoglobulin Heavy and Light Chains to Antibody Specificity for Lysozyme and Two Haptens," *The Journal of Immunology* 139(12):4135-4144.

Song, M-K. et al. (2000). "Light Chain of Natural Antibody Plays a Dominant Role in Protein Antigen Binding," *Biochemical and Biophysical Research Communications* 268(2):390-394.

Vajdos, F.F. et al. (2002). "Comprehensive Functional Maps of the Antigen-Binding Site of an Anti-ErbB2 Antibody Obtained with Shotgun Scanning Mutagenesis," *J. Mol. Biol.* 320:415-428.

Wu, H. et al. (1999). "Humanization of a Murine Monoclonal Antibody by Simultaneous Optimization of Framework and CDR Residues," *J. Mol. Biol.* 294:151-162.

Burgess, W.H. et al. (Nov. 1990). "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology* 111:2129-2138.

Harmsen, M.M. et al. (2007, e-pub. Aug. 18, 2007). "Properties, Production, and Applications of Camelid Single-Domain Antibody Fragments," *Appl. Microbiol. Biotechnol.* 77:13-22.

Lazar, E. et al. (Mar. 1988). "Transforming Growth Factor α: Mutation of Aspartic Acid 47 and Leucine 48 Results in Different Biological Activities," *Molecular and Cellular Biology* 8(3):1247-1252.

Muyldermans, S. et al. (1999). "Unique Single-Domain Antigen Binding Fragments Derived from Naturally Occurring Camel Heavy-Chain Antibodies," *Journal of Molecular Recognition* 12:131-140.

Non-Final Office Action mailed Mar. 26, 2010, for U.S. Appl. No. 11/659,009, filed Jan. 30, 2007, 18 pages.

Skolnick, J. et al. (Jan. 2000). "From Genes to Protein Structure and Function: Novel Applications of Computational Approaches in the Genomic Era," *TIBTECH* 18:34-39.

* cited by examiner

FIGURE 1

| | | | | | | | | | | | | | | | |
|---|---|---|---|---|---|---|---|---|---|---|---|---|---|---|---|
| 1 | GAC | ATC | CAG | ATG | ACC | CAG | TCT | CCA | TCC | TCT | CTG | TCT | GCA | TCT | GTA | 45 |
| 1 | Asp | Ile | Gln | Met | Thr | Gln | Ser | Pro | Ser | Ser | Leu | Ser | Ala | Ser | Val | 15 |
| 46 | GGA | GAC | CGT | GTC | ACC | ATC | ACT | TGC | CGG | GCA | AGT | CAG | AGC | ATT | GAT | 90 |
| 16 | Gly | Asp | Arg | Val | Thr | Ile | Thr | Cys | Arg | Ala | Ser | Gln | Ser | Ile | Asp | 30 |
| 91 | AGT | TAT | TTA | CAT | TGG | TAC | CAG | CAG | AAA | CCA | GGG | AAA | GCC | CCT | AAG | 135 |
| 31 | Ser | Tyr | Leu | His | Trp | Tyr | Gln | Gln | Lys | Pro | Gly | Lys | Ala | Pro | Lys | 45 |
| 136 | CTC | CTG | ATC | TAT | AGT | GCA | TCC | GAG | TTG | CAA | AGT | GGG | GTC | CCA | TCA | 180 |
| 46 | Leu | Leu | Ile | Tyr | Ser | Ala | Ser | Glu | Leu | Gln | Ser | Gly | Val | Pro | Ser | 60 |
| 181 | CGT | TTC | AGT | GGC | AGT | GGA | TCT | GGG | ACA | GAT | TTC | ACT | CTC | ACC | ATC | 225 |
| 61 | Arg | Phe | Ser | Gly | Ser | Gly | Ser | Gly | Thr | Asp | Phe | Thr | Leu | Thr | Ile | 75 |
| 226 | AGC | AGT | CTG | CAA | CCT | GAA | GAT | TTT | GCT | ACG | TAC | TAC | TGT | CAA | CAG | 270 |
| 76 | Ser | Ser | Leu | Gln | Pro | Glu | Asp | Phe | Ala | Thr | Tyr | Tyr | Cys | Gln | Gln | 90 |
| 271 | GTT | GTG | TGG | CGT | CCT | TTT | ACG | TTC | GGC | CAA | GGG | ACC | AAG | GTG | GAA | 315 |
| 91 | Val | Val | Trp | Arg | Pro | Phe | Thr | Phe | Gly | Gln | Gly | Thr | Lys | Val | Glu | 105 |
| 316 | ATC | AAA | CGG | 324 | | | | | | | | | | | | |
| 106 | Ile | Lys | Arg | | | | | | | | | | | | | |

FIGURE 3A

Marmoset Sequences

Marmoset nucleotide sequence 1 (SEQ ID No:16)
GACATCCAGATGACCCAGTCTCCATCTTCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 2 (SEQ ID No:17)
GACATCCAGATGATCCAGTCTCCATCCTCCCTGTCTGCATCTGTAGGAGACAGAGTCACCATC
ACTTGCTGGGCAAGTCAGGGTATTAGCCACTGGTTAGCCTGGTATCAGCAGAAACCAGGGAAA
GCCCCTAAGCTCCTGATCTATAGTGCATCAAATTTAGAAACAGGGGTCCCATCAAGGTTCAGT
GGAAGTGGATCCAGGACAGATTTTACTCTCACCATCAGCAGCCTGCAGCCTGAAGATATTGCA
ACATATTACTGTCAA

Marmoset nucleotide sequence 3 (SEQ ID No:18)
GACATCCAGATGACCCAGACTCCATCCTCCCTGTCTGCATCTGTAGGAGACAGAGTCACCATC
ACTTGCCGGGCAAGTCAGGGTATTAGCAGCTGGTTAGCCTGGTATCAGCAGAAACCAGGGAAA
GCCCCTAAGCTCCTGATCTATGGGGCATCAAATTTGGAAACAGGGGTCCCATCAAGATTCAGC
GGAAGTGGATCTGGGACAGATTTTACTCTCACCATCAGCAGTCTGCAGCCTGAAGATATTGCA
ACATATTACTGTCAA

Marmoset nucleotide sequence 4 (SEQ ID No:19)
GACATCCAGATGATCCAGTCTCCATCCTCCCTGTCTGCATCTGTAGGAGACAGAGTCACCATC
ACTTGCTGGGCAAGTCAGGGTATTAGCCACTGGTTAGCCTGGTATCAGCAGAAACCAGGGAAA
GCCCCTAAGCTCCTGATCTATAGTGCATCAAATTTAGGAACAGGGGTCCCATCAAGGTTCAGT
GGAAGTGGATCCAGGACAGATTTTACTCTCACCATCAGCAGCCTGCAGCCTGAAGATATTGCA
ACATATTACTGTCAA

FIGURE 3B

Marmoset nucleotide sequence 5 (SEQ ID No:20)
GACATCCAGATGACCCAGTCTCCATCTTCCCTGACTGCATCTGTAGGAGGCAAAGTCACCATC
ACTTGCCGGGCGTGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 6 (SEQ ID No:21)
GACATCCAGATGACCCAGTCTCCATCCTCCCTGTCTGCATCTGTAGGAGACAGAGTTACCATC
ACTTGCCGGGCGAGTCAGGGCATTAGTAATTATTTAGCCTGGTATCAGCAGAAACCAGGGAAA
ACTCCTAGGCTCCTGATCTATGCTGCATCCAGTTTACAAACTGGGATTCCCTCTCGGTTCAGC
GGCAGTGGATCTGGGACAGACTACACTCTCACCATCAGCAGCCTGCAGTCTGAAGATGTTGCA
ATTTATTACTGTCAA

Marmoset nucleotide sequence 7 (SEQ ID No:22)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGCTCAGC
GGCAGTGGATCTGGGACATATTTCACTCTCACCATCAGCAGCCTGCAGCCTGAAGATGCTGCA
ACTTATTACTGTCAG

Marmoset nucleotide sequence 8 (SEQ ID No:23)
GACATCCAGATGACCCAGTCTCCATCTTCCCTGACTGCATCTGTAGGAGGCAAAGTCACCATC
ACTTGCCGGGCGAGTCAGGACATTAACAAGTGGTCAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

FIGURE 3C

Marmoset nucleotide sequence 9 (SEQ ID No:24)
GACATCCAGATGACCCAGTCTCCATCTTCCCTGACTGCATCTGTAGGAGGCAAAGTCACCGTC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 10 (SEQ ID No:25)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCTTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 11 (SEQ ID No:26)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATTAAGGTTCAGC
GGCAGTGGATCTGGGACATATTTTACTCTCACCATCAGCAGCCTGCAGCCTGAAGATGCTGCA
ACTTATTACTGTCAG

Marmoset amino acid sequence 1 (SEQ ID No:27)
DIQMTQSPSSLTASVGGKVTITCRASQDINKWLAWYQQKPGTVPKPLIYEASKLQSGVPSRFS
GSGSGTYFTLTISSLQPEDAATYYCQ

Marmoset amino acid sequence 2 (SEQ ID No:28)
DIQMIQSPSSLSASVGDRVTITCWASQGISHWLAWYQQKPGKAPKLLIYSASNLETGVPSRFS
GSGSRTDFTLTISSLQPEDIATYYCQ

Marmoset amino acid sequence 3 (SEQ ID No:29)
DIQMTQTPSSLSASVGDRVTITCRASQGISSWLAWYQQKPGKAPKLLIYGASNLETGVPSRFS
GSGSGTDFTLTISSLQPEDIATYYCQ

FIGURE 3D

Marmoset amino acid sequence 4 (SEQ ID No:30)
DIQMIQSPSSLSASVGDRVTITCWASQGISHWLAWYQQKPGKAPKLLIYSASNLGTGVPSRFS
GSGSRTDFTLTISSLQPEDIATYYCQ

Marmoset amino acid sequence 5 (SEQ ID No:31)
DIQMTQSPSSLTASVGGKVTITCRACQDINKWLAWYQQKPGTVPKPLIYEASKLQSGVPSRFS
GSGSGTYFTLTISSLQPEDAATYYCQ

Marmoset amino acid sequence 6 (SEQ ID No:32)
DIQMTQSPSSLSASVGDRVTITCRASQGISNYLAWYQQKPGKTPRLLIYAASSLQTGIPSRFS
GSGSGTDYTLTISSLQSEDVAIYYCQ

Marmoset amino acid sequence 7 (SEQ ID No:33)
DIQMTQSPSSLTASVGGKVTITCRASQDINKWLAWYQQKPGTVPKPLIYEASKLQSGVPSRLS
GSGSGTYFTLTISSLQPEDAATYYCQ

Marmoset amino acid sequence 8 (SEQ ID No:34)
DIQMTQSPSSLTASVGGKVTITCRASQDINKWSAWYQQKPGTVPKPLIYEASKLQSGVPSRFS
GSGSGTYFTLTISSLQPEDAATYYCQ

Marmoset amino acid sequence 9 (SEQ ID No:35)
DIQMTQSPSSLTASVGGKVTVTCRASQDINKWLAWYQQKPGTVPKPLIYEASKLQSGVPSRFS
GSGSGTYFTLTISSLQPEDAATYYCQ

Marmoset amino acid sequence 10 (SEQ ID No:36)
DIQMTQSPSSLTASVGGKVTITCRASQDINKWLAWYQQKPGTVLKPLIYEASKLQSGVPSRFS
GSGSGTYFTLTISSLQPEDAATYYCQ

Marmoset amino acid sequence 11 (SEQ ID No:37)
DIQMTQSPSSLTASVGGKVTITCRASQDINKWLAWYQQKPGTVPKPLIYEASKLQSGVPLRFS
GSGSGTYFTLTISSLQPEDAATYYCQ

FIGURE 3E

Owl Monkey sequences

Owl Monkey nucleotide sequence 1 (SEQ ID No:38)
GACATCCAGATGACCCAGTCTCCATCCTTCCTGTCTGCATCTGCAGGAGACAGAGTCACCATC
ACCTGCCAGGTGAGTCAGGGAATTAGCAGTGAATTACTCTGGTATCAGCAGAAACCAGGGAAA
GCCCCTATGCTCTTGATCTATGCTGCAACCAAATTGCAGTCGGGAATCCCATCTCGGTTCAGT
GGCCATGGATCTGGGACAGATTTCACTCTCACCATCAGCAGCCTGCAGCCTGATGATTTTGCT
ACTTATTACTGTCAA

Owl Monkey nucleotide sequence 2 (SEQ ID No:39)
GACATCCAGATGACCCAGTCTGCATTCTCCCTGTCTGCATCTGTAGGAGACAGAGTCACCATT
ACTTGCCAGGCGAGTCAGGGCATTACCAGTGATTTAGCCTGGTATCAGCAAAAGCCAGGGAAC
GCCTCTAAGCTCCTGATCTATGAGGCATCCAGTTTACAAAGCGAGGTCCCATCAAGGTTCAGC
GGCAGTGGATCTGGGAGAGATTTTACTCTCACCATCAGCAGCCTGCAGCCTGAAGATTTTGTA
ACTTATTACTGTCAA

Owl Monkey nucleotide sequence 3 (SEQ ID No:40)
GACATCCAGATGACCCAGACTCCATCCTCCCTGTCTGCATCTGTAGGAGACAGAGTCACCATC
ACTTGCCGGGCGAGTCAAGACATTTACAATTATTTAGCCTGGTATCAGCAGAAACCAGGGAAA
ACTCCTAGGCTCTTGATCTATGCTGCATCCAGTTTGCAAACTGGGATTCCCTCTCGGTTCAGT
GGCAGTGGATCTGGGACAGACTACACTCTCACCATCAGCAGCCTGCAGCCTGATGATTTTGCC
ACTTATTACTGTCAA

Owl Monkey nucleotide sequence 4 (SEQ ID No:41)
GACATCCAGATGACCCAGACTCCATCCTCCCTGCCTGCATCTGTAGGAGACAAAGTCACCATC
ACTTGCCGGGCAAGTCAGGGTATTAGCAGCTGGTTAGCCTGGTATCAGCAGAAACCAGGGAAA
GCCCCTAAGCTCCTGATCCATAAGGCATCAAATTTGGAAACAGGGGTCCCATCAAGGTTCAGT
GGAAGTGGATCTGGGACAGATTTTACTCTCACCATCAGCAGCCTGCAGCCTGAAGATATCGCA
ACATATTACTGTCAA

FIGURE 3F

Owl Monkey nucleotide sequence 5 (SEQ ID No:42)

GACATCCAGATGACCCAGTCTCCATCTTCCCTGACTGCATCTGTAGGAGACAAAGTCACCATC
ACTTGCCGGGCAAGTCAGGGCATTAGCAATAATTTAGCCTGGTATCAGCAGAAACCAGGGAAA
GCCCCTAAGCCCCTGATCTATTATGCATCCAGTTTGCAAAGCGGGGTCCCATCAAGGTTCAGC
GGCAGTGGATCTGGGGCAGATTACACTCTCACCACCAGCAGCCTGCAGCCTGAAGATTTTGCA
ACTTATTACTGTCAA

Owl Monkey nucleotide Sequence 6 (SEQ ID No:43)

GACAACCAGATGATCCAGTCTCCATCTTCCCTGACTGCATCTGTAGGAGACAGAGTCACCATC
ACTTGCCGAGCCAGTCAGAGTATTAGCAGCTGGTTAGCCTGGTATCAGCAGAAACCAGGGACA
GTCCCTAAGCCTCTGATCTATGACGCATCCAAATTGCTAAGTGGGGTCCCATCAAGGTTCAGT
GGCTGTGGATCTGGGACAGATTTTACTCTCACCATCAGCAGCCTGCAGCCTGAAGATTTTGCA
ACTTATTACTGTCAA

Owl Monkey amino acid sequence 1 (SEQ ID No:44)

DIQMTQSPSFLSASAGDRVTITCQVSQGISSELLWYQQKPGKAPMLLIYAATKLQSGIPSRFS
GHGSGTDFTLTISSLQPDDFATYYCQ

Owl Monkey amino acid sequence 2 (SEQ ID No:45)

DIQMTQSAFSLSASVGDRVTITCQASQGITSDLAWYQQKPGNASKLLIYEASSLQSEVPSRFS
GSGSGRDFTLTISSLQPEDFVTYYCQ

Owl Monkey amino acid sequence 3 (SEQ ID No:46)

DIQMTQTPSSLSASVGDRVTITCRASQDIYNYLAWYQQKPGKTPRLLIYAASSLQTGIPSRFS
GSGSGTDYTLTISSLQPDDFATYYCQ

Owl Monkey amino acid sequence 4 (SEQ ID No:47)

DIQMTQTPSSLPASVGDKVTITCRASQGISSWLAWYQQKPGKAPKLLIHKASNLETGVPSRFS
GSGSGTDFTLTISSLQPEDIATYYCQ

Owl Monkey amino acid sequence 5 (SEQ ID No:48)

DIQMTQSPSSLTASVGDKVTITCRASQGISNNLAWYQQKPGKAPKPLIYYASSLQSGVPSRFS
GSGSGADYTLTTSSLQPEDFATYYCQ

FIGURE 3G

Owl Monkey amino acid sequence 6 (SEQ ID No:49)

DNQMIQSPSSLTASVGDRVTITCRASQSISSWLAWYQQKPGTVPKPLIYDASKLLSGVPSRFS
GCGSGTDFTLTISSLQPEDFATYYCQ

FIGURE 4

```
            D  I  Q  M  T  Q  S  P  S  S  L  S  A  S  V  G  D  R  V  T  I  T  C  R  A  S  Q
1      GACATCCAGATGACCCAGTCTCCATCCTCTCTGTCTGCATCTGTAGGAGACCGTGTCACCATCACTTGCCGGGCAAGTCA    80
1      CTGTAGGTCTACTGGGTCAGAGGTAGGAGAGACAGACGTAGACATCCTCTGGCACAGTGGTAGTGAACGGCCCGTTCAGT    80

S  I  D  S  Y  L  H  W  Y  Q  Q  K  P  G  K  A  P  K  L  L  I  Y  S  A  S  E
81     GAGCATTGATAGTTATTTACATTGGTACCAGCAGAAACCAGGGAAAGCCCCTAAGCTCCTGATCTATAGTGCATCCGAGT   160
81     CTCGTAACTATCAATAAATGTAACCATGGTCGTCTTTGGTCCCTTTCGGGGATTCGAGGACTAGATATCACGTAGGCTCA   160
                       KpnI

L  Q  S  G  V  P  S  R  F  S  G  S  G  S  G  T  D  F  T  L  T  I  S  S  L  Q  P
161    TGCAAAGTGGGGTCCCATCACGTTTCAGTGGCAGTGGATCTGGGACAGATTTCACTCTCACCATCAGCAGTCTGCAACCT   240
161    ACGTTTCACCCCAGGGTAGTGCAAAGTCACCGTCACCTAGACCCTGTCTAAAGTGAGAGTGGTAGTCGTCAGACGTTGGA   240
                 SanDI

E  D  F  A  T  Y  Y  C  Q  Q  V  V  W  R  P  F  T  F  G  Q  G  T  K  V  E  I  K
241    GAAGATTTTGCTACGTACTACTGTCAACAGGTTGTGTGGCGTCCTTTTACGTTCGGCCAAGGGACCAAGGTGGAAATCAA   320
241    CTTCTAAAACGATGCATGATGACAGTTGTCCAACACACCGCAGGAAAATGCAAGCCGGTTCCCTGGTTCCACCTTTAGTT   320

R
321    ACGG   324
321    TGCC   324
```

DOMAIN ANTIBODY CONSTRUCT

CROSS-REFERENCE TO RELATED APPLICATIONS

This application claims the benefit of U.S. Provisional Application No. 60/817,507, filed Jun. 28, 2006 and Australian Application No. 2006900456, filed Feb. 1, 2006, which are incorporated herein by reference in their entirety.

FIELD OF THE INVENTION

The present invention relates to a domain antibody construct useful for human therapy. More particularly, the present invention relates to a domain antibody construct which binds to human TNF-α and its use in the treatment of disorders characterised by TNF-α activity.

BACKGROUND OF THE INVENTION

Tumor necrosis factor alpha (TNF-α) is a cytokine that has been implicated in mediating shock and the pathophysiology of a variety of human diseases and disorders including sepsis, infections, autoimmune diseases eg. rheumatoid arthritis, Crohn's disease, ulcerative colitis and other bowel conditions, psoriasis, toxic shock, transplant rejection and graft-versus-host disease. TNF-α is produced primarily by activated macrophages and T lymphocytes, but also by neutrophils, endothelial cells, keratinocytes and fibroblasts during acute inflammatory reactions.

Because of its role in inflammation, TNF-α has emerged as an important target for inhibition in efforts to reduce the symptoms of inflammatory disorders. Various approaches to inhibition of TNF-α for the clinical treatment of disease have been pursued, including particularly the use of soluble TNF-α receptors and antibodies specific for TNF-α.

Domain Antibodies

Domain antibodies (dAb) are the smallest functioning binding units of antibodies and correspond to the variable regions of either the heavy ($V_H$) or light ($V_L$) chains of antibodies. Domain antibodies have a molecular weight of approximately 13 kDa, or less than one tenth the size of a full antibody.

In contrast to conventional antibodies, domain antibodies are well expressed in bacterial, yeast and mammalian systems. Their small size allows for higher molar quantities per gram of product, thus providing a significant increase in potency per milligram dose. In addition, dAbs can be used as building blocks to create therapeutic products such as multiple targeting dAb-containing molecules in which two or more dAbs bind to two or more distinct molecular targets, or dAbs may be incorporated into structures designed for pulmonary or oral administration.

The present inventors have now devised a novel domain antibody construct comprising an immunoglobulin variable domain linked to a constant region including a truncated $C_H1$ domain. It is postulated that the inclusion of a constant region will assist in prolonging the in vivo half-life of the dAb which is typically of a short duration.

New World Primate Immunoglobulin

Evolutionarily distant primates, such as New World primates are sufficiently similar to human to have antibodies similar to human antibodies so that the host does not generate an anti-antibody immune response when such primate-derived antibodies are introduced into a human. New World primates (infraorder-Platyrrhini) comprise at least 53 species commonly divided into two families, the Callithricidae and Cebidae. The Callithricidae consist of marmosets and tamarins. The Cebidae includes the squirrel monkey, titi monkey, spider monkey, woolly monkey, capuchin, night or owl monkey and the howler monkey.

Previous studies have characterised the expressed immunoglobulin heavy chain repertoire of the *Callithrix jacchus* marmoset (von Budingen H-C et al., Characterization of the expressed immunoglobulin IGHV repertoire in the New World marmoset *Callithrix jacchus*. Immunogenetics; 53:557-563 (2001)). Six IGHV subgroups were identified which showed a high degree of sequence similarity to their human IGHV counterparts. The framework regions were more conserved when compared to the complementarity determining regions (CDRs), with the greatest degree of variability located in CDR3. The degree of similarity between *C. jacchus* and human IGHV sequences was less than between Old World monkeys and humans.

SUMMARY OF THE INVENTION

In a first aspect, the present invention provides a domain antibody construct which binds to human TNF-α, the construct comprising:

(a) a domain antibody (dAb) which binds to human TNF-α

(b) a modified hinge region sequence;

(c) a human or primate heavy chain constant region sequence having a truncated $C_H1$ domain of not more than 20 residues, more preferably not more than 10 residues, still more preferably not more than 5 residues and even more preferably a single residue;

wherein said modified hinge region sequence contains either a deletion or a single amino acid substitution of the cysteine residue which normally facilitates disulfide bond formation between heavy and light antibody chains.

In a second aspect the present invention provides a nucleic acid sequence encoding the domain antibody construct of the first aspect of the invention.

In a third aspect the present invention provides an isolated nucleic acid molecule comprising a sequence encoding a domain antibody construct which binds human TNF-α, wherein the nucleic acid molecule comprises a nucleic acid sequence at least 60%, preferably at least 80% identical, more preferably at least 90%, 95%, 96%, 97%, 98% or 99% identical to the sequence set forth in SEQ ID No:50 or SEQ ID No:51 and most preferably, the sequence set forth in SEQ ID No:50 or SEQ ID No:51.

In a fourth aspect the present invention provides an isolated nucleic acid molecule comprising a sequence encoding a domain antibody construct which binds human TNF-α, wherein the nucleic acid molecule comprises a nucleic acid sequence which hybridises under conditions of high stringency to the nucleotide sequence set forth in SEQ ID No:50 or SEQ ID No:51.

In a fifth aspect, the invention provides a pharmaceutical composition comprising an effective amount of the domain antibody construct according to the first aspect, together with a pharmaceutically acceptable carrier or diluent.

In a sixth aspect, the present invention provides for the use of the domain antibody construct according to the first aspect of the invention in a diagnostic application for detecting human TNF-α.

In a seventh aspect, the invention provides a method for treating a disorder characterised by human TNF-α activity in a human subject, comprising administering to the subject a pharmaceutical composition according to the fifth aspect of the invention.

BRIEF DESCRIPTION OF THE FIGURES

FIG. 1 shows the amino acid (SEQ ID No:5) and nucleotide sequence (SEQ ID No:6) of the acceptor dAb.

FIGS. 3(A-G) shows the nucleotide and amino acid sequences of eleven (11) marmoset and six (6) Owl monkey Vκ gene segments.

FIG. 4 shows the acceptor dAb amino acid (SEQ ID NO:5) and nucleotide sequence (both strands) (SEQ ID NO:6 AND SEQ ID NO:68). The restriction digest sites for Kpn I and San DI which excises region including the CDR2 is indicated in the figure. CDR2 residues removed are indicated in underlined.

DETAILED DESCRIPTION OF THE INVENTION

Figure 2A:
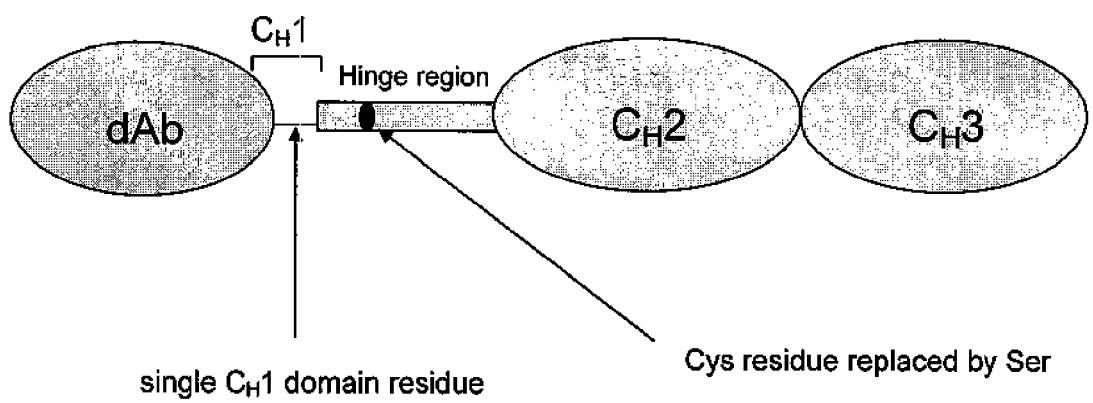
FIG. 2 shows the structure of the preferred embodiment of the domain antibody construct according to the present invention as (A) a monomer and (B) a dimer.

The present inventors have generated a domain antibody construct which binds to human TNF-α and which is postulated to exhibit low immunogenicity when administered to humans. The domain antibody construct comprises a portion corresponding to a variable domain of an immunoglobulin heavy or light chain (ie. a domain antibody (dAb)), a hinge region and a portion corresponding to a constant region of an antibody heavy chain but wherein the constant region has a truncated $C_H1$ domain. The inclusion of the constant region portion is postulated to increase the in vivo half life of the dAb as well as providing effector functions which are believed to be a component of the anti-inflammatory mechanism of anti-TNF antibodies.

In a first aspect, the present invention provides a domain antibody construct which binds to human TNF-α, the construct comprising:

(a) a domain antibody (dAb) which binds to human TNF-α
(b) a modified hinge region sequence;
(c) a human or primate heavy chain constant region sequence having a truncated $C_H1$ domain of not more than 20 residues, more preferably not more than 10 residues, still more preferably not more than 5 residues and even more preferably a single residue;

wherein said modified hinge region sequence contains either a deletion or a single amino acid substitution of the cysteine residue which normally facilitates disulfide bond formation between heavy and light antibody chains.

In a preferred embodiment the sequence of the $C_H1$ domain and the hinge region is XEPKSZDKTHTCPPCPA (SEQ ID NO:64) wherein X is valine, leucine or isoleucine and Z is absent or an amino acid other than cysteine. It is preferred that X at position one is valine and Z is serine.

In a preferred embodiment of the present invention the dAb comprises an immunoglobulin heavy or light chain variable domain, wherein said variable domain comprises at least one complementarity determining region (CDR) having a sequence derived from a New World primate wherein the CDR is selected from the group consisting of

```
YAATKLQS,       (SEQ ID No: 1)

YEASSLQS,       (SEQ ID No: 2)

YEASKLQS,       (SEQ ID No: 3)
and

YSASNLET        (SEQ ID No: 4)
```

In another preferred embodiment the CDR is CDR2.
In a preferred embodiment the dAb has a sequence selected from the group consisting of:

```
                        (Compound 145; SEQ ID No: 7)
DIQMTQSPSSLSASVGDRVTITCRASQSIDSYLHWYQQKPGKAPKLLIYS

ASNLETGVPSRFSGSGSGTDFTLTISSLQPEDFATYYCQQVVWRPFTFGQ

GTKVEIKR (Compound 123; SEQ ID No: 8)
DIQMTQSPSSLSASVGDRVTITCRASQAIDSYLHWYQQKPGKAPKLLIYS

ASNLETGVPSRFSGSGSGTDFTLTISSLQPEDFATYYCQQVVWRPFTFGQ

GTKVEIKR (Compound 100; SEQ ID No: 9)
DIQMTQSPSSLSASVGDRVTITCRASQSIDSYLHWYQQKPGKAPKLLIYS

ASNLETGVPSRFSGSGSGTDFTLTISSLLPEDFATYYCQQVVWRPFTFGQ

GTKVEIKR (Compound 196; SEQ ID No: 10)
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKR
```

-continued (Compound 134; SEQ ID No: 52)
DIQMTQSPSSLSASVGDRVTITCRASQSIDSYLHWYQQKPGKPPKLLIYS

ASNLETGVPSRFSGSGSGTDFTLTISSLQPEDFATYYCQQVVWRPFTFGQ

GTKVEIKR (Compound 137; SEQ ID No: 53)
DIQMTQSPSSLSASVGDRVTITCRASQSIDSYLHWYQQKPGKAPKLLIYS

ASNLETGVPSRFSGRGSGTDFTLTISSLQPEDFATYYCQQVVWRPFTFGQ

GTKVEIKR (Compound 121; SEQ ID No: 54)
DIQMTQSPSSLSASVGDRVTITCRASQSIDSYLHWYQQKPGKAPKLLIYS

ASNLETGVPSRFSGSGSGTDFTLTISSLVPEDFATYYCQQVVWRPFTFGQ

GTKVEIKR;
and a sequence at least 95%, more preferably at least 96%, 97%, 98% or 99% identical to one of these sequences.

In a further preferred embodiment the constant region comprises $C_H2$ and $C_H3$ domains which together have the following sequence:

(SEQ ID NO: 63)
PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK;

or an amino acid sequence which is at least 60%, preferably at least 80% identical, more preferably at least 90%, 95%, 96%, 97%, 98% or 99% identical thereto.

In another preferred embodiment the domain antibody construct comprises an amino acid sequence which is at least 60%, preferably at least 80% identical, more preferably at least 90%, 95%, 96%, 97%, 98% or 99% identical to the sequence set forth in SEQ ID No:11, and most preferably the sequence set forth in SEQ ID No:11.

The term "binds to" as used herein, is intended to refer to the binding of an antigen by an immunoglobulin variable region with a dissociation constant ($K_d$) of 1 µM or lower as measured by surface plasmon resonance analysis using, for example a BIAcore™ surface plasmon resonance system and BIAcore™ kinetic evaluation software (eg. version 2.1). The affinity or dissociation constant ($K_d$) for a specific binding interaction is preferably about 500 nM or lower, more preferably about 300 nM or lower and preferably at least 300 nM to 50 pM, 200 nM to 50 pM, and more preferably at least 100 nM to 50 pM, 75 nM to 50 pM, 10 nM to 50 pM. The term "dAb" as used herein refers to an antibody single variable domain ($V_H$ or $V_L$) polypeptide that specifically binds antigen.

In a further preferred embodiment of the present invention the domain antibody construct forms a homo- or heterodimer with another domain antibody construct according to the present invention. Dimerisation can increase the strength of antigen binding, wherein the strength of binding is related to the sum of the binding affinities of the multiple binding sites. To facilitate dimer formation, the hinge region of the domain antibody construct comprises at least one, and preferably two, cysteine residues.

In a particularly preferred embodiment of the present invention, the domain antibody construct forms a homodimer with an identical domain antibody construct.

Accordingly in another aspect the present invention provides a dimeric domain antibody construct which binds to human TNF-α wherein the dimer consists of two domain antibody constructs according to the present invention.

It is preferred that the dimeric domain antibody construct is a homodimer and it is particularly preferred that the domain antibody constructs making up the homodimer comprise an amino acid sequence which is at least 60%, preferably at least 80% identical, more preferably at least 90%, 95%, 96%, 97%, 98% or 99% identical to the sequence set forth in SEQ ID No:11, and most preferably the sequence set forth in SEQ ID No:11.

In a second aspect the present invention provides a nucleic acid sequence encoding the domain antibody construct of the first aspect of the invention.

In a third aspect the present invention provides an isolated nucleic acid molecule comprising a sequence encoding a domain antibody construct which binds human TNF-α, wherein the nucleic acid molecule comprises a nucleic acid sequence at least 60%, preferably at least 80% identical, more preferably at least 90%, 95%, 96%, 97%, 98% or 99% identical to the sequence set forth in SEQ ID No:50 or SEQ ID No:51 and most preferably, the sequence set forth in SEQ ID No:50 or SEQ ID No:51.

In a fourth aspect the present invention provides an isolated nucleic acid molecule comprising a sequence encoding a domain antibody construct which binds human TNF-α, wherein the nucleic acid molecule comprises a nucleic acid sequence which hybridises under conditions of high stringency to the nucleotide sequence set forth in SEQ ID No:50 or SEQ ID No:51.

In determining whether or not two polypeptide sequences fall within percentage identity limits, those skilled in the art will be aware that it is necessary to conduct a side-by-side comparison or multiple alignment of sequences. In such comparisons or alignments, differences will arise in the positioning of non-identical residues, depending upon the algorithm used to perform the alignment. In the present context, reference to a 'percentage identity' or 'similarity' between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America (Devereaux et al, 1984). The GAP programme utilizes the algorithm of Needleman and Wunsch (1970) to maximise the number of identical/similar residues and to minimise the number and length of sequence gaps in the alignment. Alternatively or in addition, wherein more than two amino acid sequences are being compared, the Clustal W programme of Thompson et al, (1994) is used.

In determining whether or not two nucleotide sequences fall within these percentage limits, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, Nucl. Acids Res., 12:387-395, 1984).

High stringency preferably involves hybridisation under conditions of 65° C. and 0.1×SSC {1×SSC=0.15 M NaCl, 0.015 M Na$_3$ Citrate pH 7.0}.

In one embodiment, the invention is further based on a method for amplification of New World primate immunoglobulin variable region genes, for example by polymerase chain reaction (PCR) from nucleic acid extracted from New World primate lymphocytes using primers specific for heavy and light chain variable region gene families. For example, information regarding the boundaries of the variable domains of heavy and light chain genes ($V_H$ and $V_L$ respectively) can be used to design PCR primers that amplify the variable domain from a cloned heavy or light chain coding sequence encoding an antibody known to bind a given antigen. The amplified variable region is then inserted either alone or as a fusion with another polypeptide sequence for the human or primate constant region sequence of the invention into a suitable expression vector for production of the domain antibody construct of the invention. Suitable expression vectors will be familiar to those skilled in the art.

The repertoire of $V_H$, $V_L$ and constant region domains can be a naturally occurring repertoire of immunoglobulin sequences or a synthetic repertoire. A naturally occurring repertoire is one prepared, for example, from immunoglobulin-expressing cells harvested from one or more primates. Such repertoires can be naïve ie. prepared from newborn immunoglobulin expressing cells, or rearranged ie. prepared from, for example, adult primate B cells. If desired, clones identified from a natural repertoire, or any repertoire that bind the target antigen are then subject to mutagenesis and further screening in order to produce and select variants with improved binding characteristics.

Synthetic repertoires of single immunoglobulin variable domains are prepared by artificially introducing diversity into a cloned variable domain.

A repertoire of $V_H$ and $V_L$ domains can be screened for desired binding specificity and functional behaviour by, for example phage display. Methods for the construction of bacteriophage display libraries and lambda phage expression libraries are well known in the art. The phage display technique has been described extensively in the art and examples of methods and compounds for generating and screening such libraries and affinity maturing the products of them can be found in, for example, Barbas et al. (1991) PNAS 88:7978-7982; Clarkson et al. (1991) Nature 352:624-628; Dower et al. PCT. 91/17271, U.S. Pat. No. 5,427,908, U.S. Pat. No. 5,580,717 and EP 527,839; Fuchs et al. (1991) Bio/Technology 9:1370-1372; Garrad et al. (1991) Bio/Technology 9:1373-1377; Garrard et al. PCT WO 92/09690; Gram et al. (1992) PNAS 89:3576-3580; Griffiths et al. (1993) EMBO J 12:725-734; Griffiths et al. U.S. Pat. No. 5,885,793 and EP 589,877; Hawkins et al. (1992) J Mol Biol 226:889-896; Hay et al. (1992) Hum Antibod Hybridomas 3:81-85; Hoogenboom et al. (1991) Nuc Acid Res 19:4133-4137; Huse et al. (1989) Science 246:1275-1281; Knappik et al. (2000) J Mol Biol 296:57-86; Knappik et al. PCT WO 97/08320; Ladner et al. U.S. Pat. No. 5,223,409, U.S. Pat. No. 5,403,484, U.S. Pat. No. 5,571,698, U.S. Pat. No. 5,837,500 and EP 436,597; McCafferty et al. (1990) Nature 348:552-554; McCafferty et al. PCT. WO 92/01047, U.S. Pat. No. 5,969,108 and EP 589,877; Salfeld et al. PCT WO 97/29131, U.S. Provisional Application No. 60/126,603; and Winter et al. PCT WO 92/20791 and EP 368,684.

Recombinant libraries expressing the repertoire of $V_H$ and $V_L$ domains can be expressed on the surface of microorganisms eg. yeast or bacteria (see PCT publications WO 99/36569 and 98/49286).

The domain antibody construct of the invention may be produced by recombinant means, including from eukaryotic expression systems including, for example, yeast, higher plant, insect and mammalian cells, as well as fungi and virally-encoded expression systems, as described herein or as known in the art.

The domain antibody constructs of the present invention can be prepared using an S antibody encoding nucleic acid to provide transgenic plants and cultured plant cells (e.g., but not limited to tobacco and maize) that produce such constructs in the plant parts or in cells cultured therefrom. As a non-limiting example, transgenic tobacco leaves expressing recombinant proteins have been successfully used to provide large amounts of recombinant proteins, e.g., using an inducible promoter (see, e.g., Cramer et al., Curr. Top. Microbol. Immunol. 240:95-118 1999) and references cited therein. Also, transgenic maize has been used to express mammalian proteins at commercial production levels, with biological activities equivalent to those produced in other recombinant systems or purified from natural sources (see, e.g., Hood et al., Adv. Exp. Med. Biol. 464:127-147 1999 and references cited therein). Antibodies have also been produced in large amounts from transgenic plant seeds including antibody fragments, such as single chain antibodies (scFv's), including tobacco seeds and potato tubers (see, e.g., Conrad et al., Plant Mol. Biol. 38:101-109 1998 and reference cited therein). Thus, the domain antibody constructs of the present invention can also be produced using transgenic plants, according to known methods (see also, e.g., Fischer et al., Biotechnol. Appl. Biochem. 30:99-108 October, 1999: Ma & Hein., Trends Biotechnol. 13:522-7 1995; Ma et al., Plant Physiol. 109:341-6 1995; Whitelam et al., Biochem. Soc. Trans. 22:940-944 1994; and references cited therein; each of the above references is entirely incorporated herein by reference).

The domain antibody constructs of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody constructs of the present invention can be glycosylated or can be non-glycosylated, with glycosylated preferred. Such methods are described in many standard laboratory manuals Sambrook, et al., Molecular Cloning: A Laboratory Manual, $2^{nd}$ Edition, Cold Spring Harbor, N.Y. 1989, Sections 17.37-17.42; Ausubel et al, eds. Current Protocols in Molecular Biology 1987-1993, Chapters 10, 12, 13, 16, 18 and 20, Colligan et al., Current Protocols in Protein Science, John Wiley & Sons, NY, N.Y. 1997-2001, Protein Science, Chapters 12-14, all entirely incorporated herein by reference.

In one expression system the recombinant peptide/protein library is displayed on ribosomes (for examples see Roberts, R W and Szostak, J. W. 1997 Proc. Natl. Acad. Sci. USA. 94:12297-123202 and PCT Publication No. WO98/31700). Thus another example involves the generation and in vitro transcription of a DNA library (eg of antibodies or derivatives preferably prepared from immunised cells, but not so limited), translation of the library such that the protein and "immunised" mRNAs stay on the ribosome, affinity selection (eg by binding to RSP), mRNA isolation, reverse translation and subsequent amplification (eg by polymerase chain reaction or related technology). Additional rounds of selection and amplification can be coupled as necessary to affinity maturation through introduction of somatic mutation in this system or by other methods of affinity maturation as known in the state of the art.

Another example sees the application of emulsion compartmentalisation technology to the generation of the domain antibodies of the invention. In emulsion compartmentalisation, in vitro and optical sorting methods are combined with co-compartmentalisation of translated protein and its nucleotide coding sequence in aqueous phase within an oil droplet in an emulsion (see PCT publications no's WO 99/026711 and WO 00/40712).

The CDR sequences may be obtained from several sources, for example, databases such as The National Centre for Biotechnology Information protein and nucleotide databases www.ncbi.nlm.nih.gov, The Kabat Database of Sequences of Proteins of Immunological Interest www.kabatdatabase.com, or the IMGT database www.imgt.cines.fr. Alternatively, the CDR regions can be predicted from the $V_H$ and $V_L$ domain repertoire (see for example Kabat E A and Wu T T Attempts to locate complementarity determining residues in the variable positions of light and heavy chains. Ann. NY Acad. Sci. 190:382-393 (1971)). The CDR sequence may be a genomic DNA or a cDNA.

There are a number of ways in which a replacement CDR may be grafted into a variable region sequence and such methods will be familiar to those skilled in the art. The preferred method of the present invention involves replacement of the CDR2 in the variable region (or dAb) via primer directed mutagenesis. This method consists of annealing a synthetic oligonucleotide encoding a desired mutation(s) to a target region where it serves as a primer for initiation of DNA synthesis in vitro, extending the oligonucleotide by a DNA polymerase to generate a double-stranded DNA that carries the desired mutation, and ligating and cloning the sequence into an appropriate expression vector.

In a preferred embodiment of the present invention, the New World primate CDR sequence is grafted into a variable region sequence which is of low immunogenicity in humans.

By reference to the term "low immunogenicity" it is meant that the domain antibody construct or antigen-binding portion thereof, does not raise an antibody response in a human of sufficient magnitude to reduce the effectiveness of continued administration of the domain antibody construct for a sufficient time to achieve therapeutic efficacy.

Preferably, the variable region sequence into which the New World primate CDR is grafted is the "dAb acceptor sequence" (designated Compound 128), in FIG. 1. The dAb acceptor sequence consists of the amino acid sequence set forth in SEQ ID No:5:

(SEQ ID No: 5)
DIQMTQSPSSLSASVGDRVTITCRASQSIDSYLHWYQQKPGKAPKLLIYS

ASELQSGVPSRFSGSGSGTDFTLTISSLQPEDFATYYCQQVVWRPFTFGQ

GTKVEIKR.

This sequence is encoded by the nucleotide sequence set forth in SEQ ID No:6:

(SEQ ID No: 6)
GAC ATC CAG ATG ACC CAG TCT CCA TCC TCT CTG TCT

GCA TCT GTA GGA GAC CGT GTC ACC ATC ACT TGC CGG

GCA AGT CAG AGC ATT GAT AGT TAT TTA CAT TGG TAC

CAG CAG AAA CCA GGG AAA GCC CCT AAG CTC CTG ATC

TAT AGT GCA TCC GAG TTG CAA AGT GGG GTC CCA TCA

CGT TTC AGT GGC AGT GGA TCT GGG ACA GAT TTC ACT

CTC ACC ATC AGC AGT CTG CAA CCT GAA GAT TTT GCT

ACG TAC TAC TGT CAA CAG GTT GTG TGG CGT CCT TTT

ACG TTC GGC CAA GGG ACC AAG GTG GAA ATC AAA CGG

In one preferred embodiment of the present invention, a marmoset New World primate CDR sequence YSASNLET (SEQ ID No:4) is grafted into the variable region dAb acceptor sequence so as to replace the CDR2 sequence (YSASELQS; SEQ ID No:55) of the dAb acceptor sequence to produce the following dAb (designated Compound 145):

Compound 145

(SEQ ID No: 7)
DIQMTQSPSSLSASVGDRVTITCRASQSIDSYLHWYQQKPGKAPKLLIYS

ASNLETGVPSRFSGSGSGTDFTLTISSLQPEDFATYYCQQVVWRPFTFGQ

GTKVEIKR

Thus, in one preferred embodiment, the dAb of the domain antibody construct which binds to human TNF-α, comprises the amino acid sequence set forth in SEQ ID No:7.

It is within the scope of the present invention, that the variable region sequence (dAb) of the domain antibody construct may be further subject to affinity maturation in order to improve its antigen binding characteristics. This may necessitate the modification of certain amino acid residues within CDR1, CDR3 or framework of the domain antibody construct.

For example, SEQ ID No:7 was affinity matured as set out in the Materials and Methods and tested for TNF-α-binding. In a further preferred embodiment, the variable region (dAb) of the domain antibody construct which binds to human TNF-α comprises the amino acid sequence of SEQ ID No:8 or SEQ ID No:9. These have been designated Compound 123 and Compound 100 respectively, and their sequences are shown below:

Compound 123

(SEQ ID No: 8)
DIQMTQSPSSLSASVGDRVTITCRASQAIDSYLHWYQQKPGKAPKLLIYS

ASNLETGVPSRFSGSGSGTDFTLTISSLQPEDFATYYCQQVVWRPFTFGQ

GTKVEIKR

Compound 100

```
                                      (SEQ ID No: 9)
DIQMTQSPSSLSASVGDRVTITCRASQSIDSYLHWYQQKPGKAPKLLIYS

ASNLETGVPSRFSGSGSGTDFTLTISSLLPEDFATYYCQQVVWRPFTFGQ

GTKVEIKR
```

In a particularly preferred embodiment, the variable region (dAb) of the domain antibody construct which binds to human TNF-α comprises the amino acid sequence of SEQ ID No: 10. This has been designated Compound 196 and the sequence is provided below:

Compound 196

```
                                      (SEQ ID No: 10)
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKR
```

It will be appreciated by persons skilled in the art that the constant region sequence of the domain antibody construct may be derived from human or primate sequences. The primate sequence may be New World primate or an Old World primate sequence. Suitable Old World primates include chimpanzee, or other hominid ape eg. gorilla or orangutan, which because of their close phylogenetic proximity to humans, share a high degree of homology with the human constant region sequence. Preferably, the constant region is derived from a human antibody sequence. Examples of such sequences can be found in The National Centre for Biotechnology Information protein and nucleotide databases www.ncbi.nlm.nih.gov, and The Kabat Database of Sequences of Proteins of Immunological Interest www.kabatdatabase.com, or the IMGT database www.imgt.cines.fr.

In designing the domain antibody construct of the present invention, the inventors have truncated the $C_H1$ domain of the constant (Fc) region. A minimal number of $C_H1$ domain residues have been retained in order to provide flexibility in the domain antibody construct around the hinge region. Preferably, at least 20 C-terminal amino acid residues of the $C_H1$ domain are retained, more preferably at least 10 amino acids, still more preferably at least 5 amino acids, even more preferably a single amino acid residue.

Figure 2B:
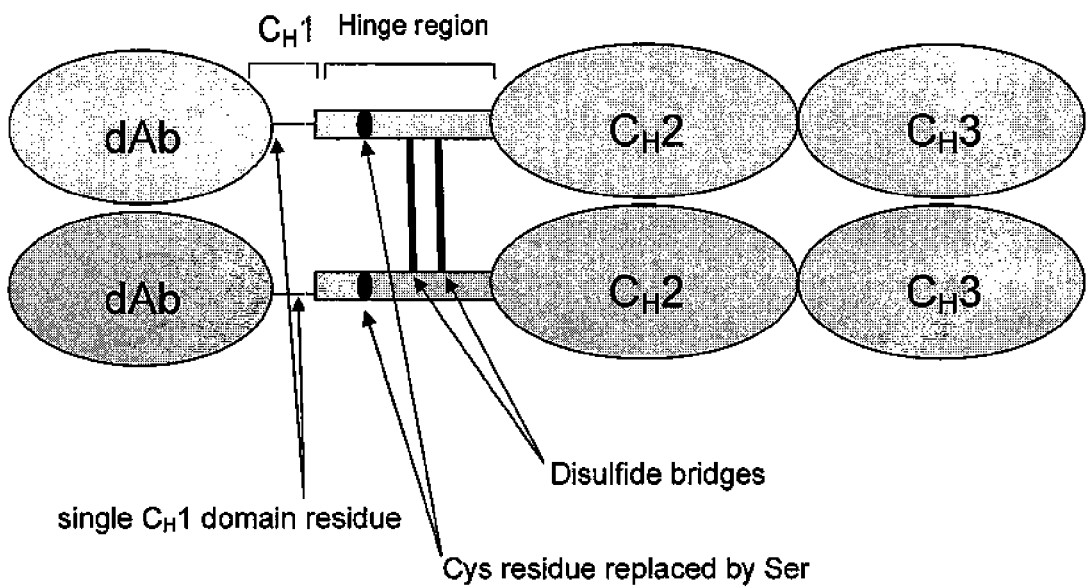
Figure 5:
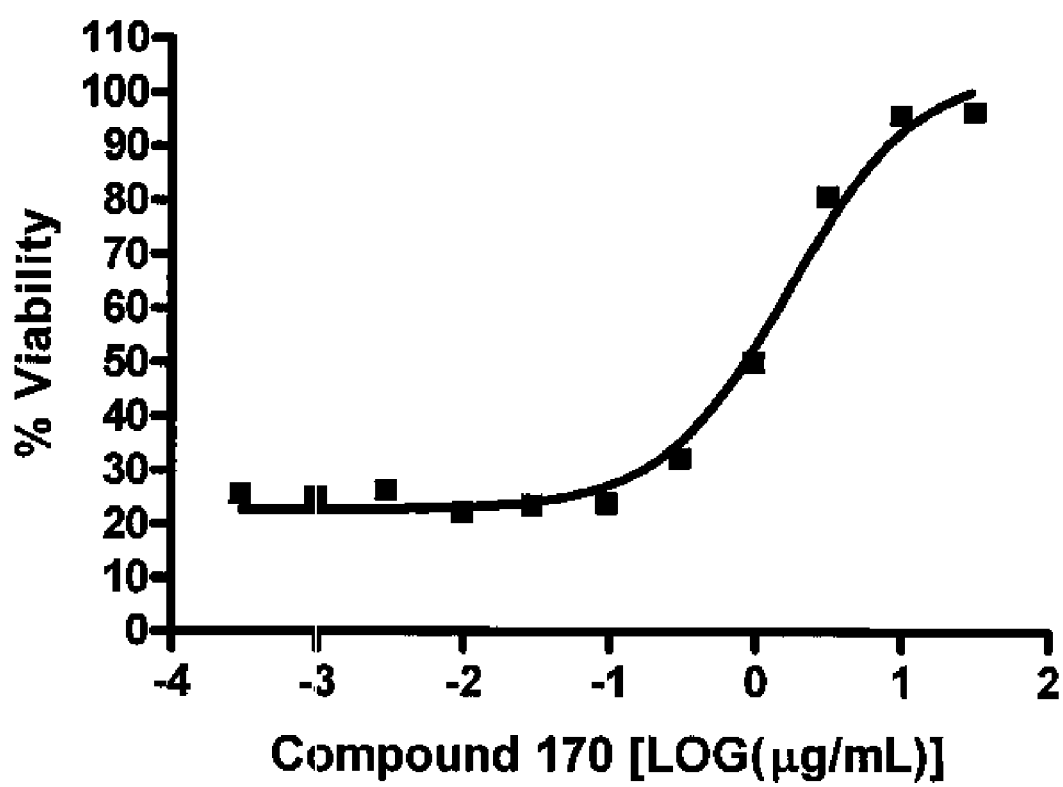
FIG. 5 shows the ability of Compound 170 (SEQ ID No:11) to neutralise TNF-α mediated cytotoxicity in a murine L929 cell viability assay.

Thus, in a preferred embodiment, the domain antibody construct has a format comprising dAb-C terminal $C_H1$ domain residue-hinge region-$C_H2$ domain-$C_H3$ domain as illustrated schematically in FIG. 2.

In a particularly preferred embodiment, the domain antibody construct has the amino acid sequence set forth in SEQ ID No:11. This has been designated Compound 170.

Compound 170

```
                                      (SEQ ID No: 11)
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKRVEPKSSDKTHTCPPCPAPELLGGPSVFLFPPKPKDTLMISRT

PEVTCVVVDVSHEDPEVKFNWYVDGVEVHNAKTPKREEQYNSTYRVVSVL

TVLHQDWLNGKEYKCKVSNKALPAPIEKTISKAKGQPREPQVYTLPPSRD
```
-continued
```
ELTKNQVSLTCLVKGFYPSDIAVEWESNGQPENNYKTTPPVLDSDGSFFL

YSKLTVDKSRWQQGNVFSCSVMHEALHNHYTQKSLSLSPGK
```

The hinge region of the naturally occurring immunoglobulin contains a cysteine (C) side chain which facilitates the formation of a disulfide bond between the $C_H1$ domain of the heavy chain and the constant domain of the light chain. Because the construct comprises only a single variable domain and thus leaves a potentially reactive unpaired cysteine residue, the cysteine residue has been substituted with an amino acid residue which prevents disulfide bond formation. The potential consequences of having an unpaired cysteine may include reduced protein expression due to aggregation and misfolding of the construct.

It is to be understood that any hinge region sequence derived from any of the antibody classes would be appropriate for use in the present invention. It is preferred however, that the hinge region is derived from the antibody subclass $IgG_1$. Preferably, the hinge region is based on the naturally occurring sequence of the hinge region of $IgG_1$ and comprises the sequence EPKSSDKTHTCPPCPA (SEQ ID No:12). In this sequence, the Cys which normally occurs at position 5 is replaced by the underlined bolded Ser residue.

Preferably, the C-terminal amino acid residue of the $C_H1$ domain is derived from IgG1. More preferably, the $C_H1$ residue is a valine (V) residue or a conservative amino acid substitution such as leucine (L) or isoleucine (I). This residue is located immediately proximal to the hinge region and assists in increasing the flexibility of the construct around the hinge region.

Sequences of the $C_H2$ and $C_H3$ domains are preferably derived from Swissprot database accession number PO1857:

```
                                      (SEQ ID No: 63)
PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK.
```

The domain antibody construct may be derivatised or linked to another functional molecule. For example, the domain antibody construct can be functionally linked by chemical coupling, genetic fusion, noncovalent association or otherwise, to one or more other molecular entities, such as another antibody, a detectable agent, a cytotoxic agent, a pharmaceutical agent, and/or a protein or peptide that can mediate association of the antibody or antibody-binding portion with another molecule (such as a streptavidin core region or a polyhistidine tag).

Useful detectable agents with which the domain antibody construct may be derivatised include fluorescent compounds. Exemplary fluorescent detectable agents include fluorescein, fluorescein isothiocyanate, rhodamine, 5-dimethylamine-1-napthalenesulfonyl chloride, phycoerythrin and the like. The domain antibody construct may also be derivatised with detectable enzymes such as alkaline phosphatase, horseradish peroxidase, glucose oxidase and the like. When the domain antibody construct is derivatized with a detectable enzyme, it is detected by adding additional reagents that the enzyme uses to produce a detectable reaction product. The domain antibody construct may also be derivatised with biotin, and detected through indirect measurement of avidin or streptavidin binding.

The domain antibody construct according to the invention may be linked to one or more molecules which provide increased half-life and resistance to degradation without loss in activity (eg binding affinity) in vivo. These molecules may be linked to the domain antibody construct via a linker so that they do not interfere/sterically hinder the antigen binding site. These adduct molecules include for example dAbs directed to an endogenous molecule as described in US patent application 20050271663. Typically, such adduct molecules are polypeptides or fragments of polypeptides which occur naturally in vivo and which resist degradation or removal by endogenous mechanisms. Molecules which increase half life may be selected from the following:

(a) proteins from the extracellular matrix, eg. collagen, laminin, integrin and fibronectin;
(b) proteins found in blood, eg. fibrin α-2 macroglobulin, serum albumin, fibrinogen A, fibrinogen B, serum amyloid protein A, heptaglobin, protein, ubiquitin, uteroglobulin, β-2 microglobulin, plasminogen, lysozyme, cystatin C, alpha-1-antitrypsin and pancreatic kypsin inhibitor;
(c) immune serum proteins, eg. IgE, IgG, IgM;
(d) transport proteins, eg. retinol binding protein, α-1 microglobulin;
(e) defensins, eg. beta-defensin 1, neutrophil defensins 1, 2 and 3;
(f) proteins found at the blood brain barrier or in neural tissues, eg. melanocortin receptor, myelin, ascorbate transporter;
(g) transferrin receptor specific ligand-neuropharmaceutical agent fusion proteins (see U.S. Pat. No. 5,977,307); brain capillary endothelial cell receptor, transferrin, transferrin receptor, insulin, insulin-like growth factor 1 (IGF 1) receptor, insulin-like growth factor 2 (IGF 2) receptor, insulin receptor;
(h) proteins localised to the kidney, eg. polycystin, type IV collagen, organic anion transporter K1, Heymann's antigen;
(i) proteins localised to the liver, eg. alcohol dehydrogenase, G250;
(j) blood coagulation factor X;
(k) α-1 antitrypsin;
(l) HNF 1α;
(m) proteins localised to the lung, eg. secretory component (binds IgA);
(n) proteins localised to the heart, eg. HSP 27;
(o) proteins localised to the skin, eg, keratin;
(p) bone specific proteins, such as bone morphogenic proteins (BMPs) eg. BMP-2, -4, -5, -6, -7 (also referred to as osteogenic protein (OP-1) and -8 (OP-2);
(q) tumour specific proteins, eg. human trophoblast antigen, herceptin receptor, oestrogen receptor, cathepsins eg cathepsin B (found in liver and spleen);
(r) disease-specific proteins, eg. antigens expressed only on activated T-cells: including LAG-3 (lymphocyte activation gene); osteoprotegerin ligand (OPGL) see Kong Y Y et al Nature (1999) 402, 304-309; OX40 (a member of the TNF receptor family, expressed on activated T cells and the only costimulatory T cell molecule known to be specifically up-regulated in human T cell leukaemia virus type-I (HTLV-I)-producing cells—see Pankow R et al J. Immunol. (2000) Jul. 1; 165(1):263-70; metalloproteases (associated with arthritis/cancers), including CG6512 Drosophila, human paraplegin, human FtsH, human AFG3L2, murine ftsH; angiogenic growth factors, including acidic fibroblast growth factor (FGF-1), basic fibroblast growth factor (FGF-2), Vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PlGF), midkine platelet-derived growth factor-BB (PDGF), fractalkine;
(s) stress proteins (heat shock proteins); and
(t) proteins involved in Fc transport.

The present invention also extends to a PEGylated domain antibody construct which provides increased half-life and resistance to degredation without a loss in activity (e.g. binding affinity) relative to non-PEGylated antibody polypeptides.

The domain antibody construct can be coupled, using methods known in the art, to polymer molecules (preferably PEG) useful for achieving the increased half-life and degradation resistance properties. Polymer moieties which can be utilised in the invention can be synthetic or naturally occurring and include, but not limited to straight or branched chain polyalkylene, polyalkenylene or polyoxyalkylene polymers, or a branched or unbranched polysaccharide such as a homo- or heteropolysaccharide. Preferred examples of synthetic polymers which can be used in the invention include straight or branched chain poly(ethylene glycol) (PEG), poly(propylene glycol), or poly(vinyl alcohol) and derivatives or substituted forms thereof. Particularly preferred substituted polymers for linkage to the domain antibody construct include substituted PEG, including methoxy(polyethylene glycol). Naturally occurring polymer moieties which can be used in addition to or in place of PEG include lactose, amylose, dextran, or glycogen, as well as derivatives thereof which would be recognised by persons skilled in the art.

The polymer (PEG) molecules useful in the invention can be attached to the domain antibody construct using methods which are well known in the art. The first step in the attachment of PEG or other polymer moieties to the domain antibody construct of the invention is the substitution of the hydroxyl end-groups of the PEG polymer by electrophile-containing functional groups. Particularly, PEG polymers are attached to either cysteine or lysine residues present in the domain antibody construct monomers or multimers. The cysteine and lysine residues can be naturally occurring, or can be engineered into the domain antibody construct molecule.

Pegylation of the domain antibody constructs of the invention may be accomplished by any number of means (see for example Kozlowski-A & Harris-J M (2001) Journal of Controlled Release 72:217). PEG may be attached to the domain antibody construct either directly or by an intervening linker. Linkerless systems for attaching polyethylene glycol to proteins is described in Delgado et al., (1992), Crit. Rev. Thera. Drug Carrier Sys. 9:249-304 Francis et al., (1998), Intern. J. Hematol. 68:1-18; U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride. Following reaction of amino acid residues with tresylated MPEG, polyethylene glycol is directly attached to the amine groups. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460 discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins are described in WO 98/32466, the entire disclosure of which is incorporated herein by reference.

In a particularly preferred embodiment of the present invention the domain antibody construct is coupled directly to polyethylene glycol via a lysine residue. In yet another preferred embodiment of the present invention, the domain antibody construct is coupled directly to PEG via a cysteine residue. The unpaired cysteine residue could pre-exist in the sequence, could be added by incorporating a cysteine residue in, for example, the C-terminus of the domain antibody construct. Alternatively, attachment of the PEG to the domain antibody construct could be facilitated via a disulphide bonded cysteine such as that described in US20060210526.

Other derivatized forms of polymer molecules include, for example, derivatives which have additional moieties or reactive groups present therein to permit interaction with amino acid residues of the domain antibody constructs described herein. Such derivatives include N-hydroxylsuccinimide (NHS) active esters, succinimidyl propionate polymers, and sulfhydryl-selective reactive agents such as maleimide, vinyl sulfone, and thiol. PEG polymers can be linear molecules, or can be branched wherein multiple PEG moieties are present in a single polymer.

The reactive group (e.g., MAL, NHS, SPA, VS, or Thiol) may be attached directly to the PEG polymer or may be attached to PEG via a linker molecule.

The size of polymers useful in the invention can be in the range of 500 Da to 60 kDa, for example, between 1000 Da and 60 kDa, 10 kDa and 60 kDa, 20 kDa and 60 kDa, 30 kDa and 60 kDa, 40 kDa and 60 kDa, and up to between 50 kDa and 60 kDa. The polymers used in the invention, particularly PEG, can be straight chain polymers or may possess a branched conformation.

In a further embodiment, the domain antibody construct according to the first aspect may be multimerised, as for example, hetero- or homodimers, hetero- or homotrimers, hetero- or homotetramers, or higher order hetero- or homo-multimers. Multimerisation can increase the strength of antigen binding, wherein the strength of binding is related to the sum of the binding affinities of the multiple binding sites.

In a fifth aspect, the invention provides a pharmaceutical composition comprising an effective amount of the domain antibody construct according to the first aspect, together with a pharmaceutically acceptable carrier or diluent.

A "pharmaceutically acceptable carrier" includes any and all solvents, dispersion media, coatings, antibacterial and antifungal agents, isotonic and absorption delaying agents, and the like which are physiologically compatible. Examples of pharmaceutically acceptable carriers include one or more of water, saline, phosphate buffered saline, dextrose, glycerol, ethanol, and the like as well as combinations thereof. In many cases it will be preferable to include isotonic agents, for example, sugars, polyalcohols such as mannitol, sorbitol, or sodium chloride in the composition. Pharmaceutically acceptable substances such as minor amounts of auxiliary substances such as wetting or emulsifying agents, preservatives or buffers.

The composition may be in a variety of forms, including liquid, semi-solid and solid dosage forms, such as liquid solutions (eg inhalable, injectable and infusible solutions), dispersions or suspensions, tablets, pills, powders, liposomes and suppositories. Preferably, the composition is in the form of an injectable solution for immunization. The administration may be intravenous, intra-arterial, subcutaneous, intraperitoneal, or intramuscular.

Therapeutic compositions typically must be sterile and stable under the conditions of manufacture and storage. The compositions can be formulated as a solution, microemulsion, dispersion, liposome, or other ordered structure suitable to high drug concentration. The proper fluidity of a solution can be maintained by for example, use of a coating such as lecithin and/or surfactants. Sterile injectable solutions can be prepared by incorporating the active compound (ie. domain antibody construct) in the required amount into an appropriate solvent with one or a combination of ingredients listed above, followed by filtered sterilisation.

The composition may also be formulated as a sterile powder for the preparation of sterile injectable solutions.

In certain embodiments the active compound may be prepared with a carrier that will protect the compound against rapid release, such as a controlled release formulation, including implants, transdermal patches, and microencapsulated delivery systems. Compatible polymers may be used such as ethylene vinyl acetate, polyanhydrides, polyglycolic acid, collagen, polyorthoesters and polylactic acid.

The composition may also be formulated for oral administration. In this embodiment, the domain antibody construct may be enclosed in a hard or soft shell gelatin capsule, compressed into tablets, or incorporated directly into the subject's diet.

Formulations that allow for pulmonary, rectal, transdermal, intrathecal and intraocular administration will be familiar to persons skilled in the art.

Supplementary active compounds can also be incorporated into the composition. The domain antibody construct may be co-formulated with and/or co-administered with one or more additional therapeutic agents eg. soluble TNF-$\alpha$ receptor or a chemical agent that inhibits human TNF-$\alpha$ production, or antibodies that bind other targets such as cytokines or cell surface molecules. Alternatively, it may be co-administered with a soluble immunochemical reagent such as protein A, C, G or L.

An effective amount may include a therapeutically effective amount or prophylactically effective amount of the domain antibody construct of the invention. A therapeutically effective amount refers to an amount effective at dosages and for periods of time necessary, to achieve the desired therapeutic result. A prophylactically effective amount refers to an amount effective, at dosages and for periods of time necessary, to achieve the desired prophylactic result. Because a prophylactic dose is administered to a subject prior to or at an earlier stage of disease, the prophylactically effective amount may be less than the therapeutically effective amount.

In a sixth aspect, the present invention provides for the use of the domain antibody construct according to the first aspect of the invention in a diagnostic application for detecting human TNF-$\alpha$.

For example, the anti-human TNF-$\alpha$ domain antibody construct according to the invention can be used to detect human TNF-$\alpha$ for example in a biological sample, such as serum or plasma using a conventional immunoassay, such as an enzyme linked immunosorbent assay (ELISA), a radioimmunoas say (RIA) or tissue immunohistochemistry. The anti-human TNF-α domain antibody construct according to the invention can be assayed in biological fluids by a competition immunoassay using recombinant human TNF-α standards labelled with a detectable substance and an unlabelled anti-human TNF-α antibody.

The anti-human TNF-α domain antibody construct according to the invention may also be used to detect TNF-α from species other than humans such as non-human primates including cynomolgus, chimpanzee, marmoset, rhesus and other species such as dog, rat, mouse, rabbit, cat, pig, bovine.

The anti-human TNF-α domain antibody construct according to the invention may also be used in cell culture applications where it is desired to inhibit TNF-α activity.

In a seventh aspect, the invention provides a method for treating a disorder characterised by human TNF-α activity in a human subject, comprising administering to the subject a pharmaceutical composition according to the fifth aspect of the invention.

A disorder characterised by human TNF-α activity is intended to include diseases and other disorders in which the presence of TNF-α in a subject suffering from the disorder has been shown to be or is suspected of being either responsible for the pathophysiology of the disorder or a factor which contributes to a worsening of the disorder. Preferably, the disorder characterised by human TNF-α activity is selected from the group consisting of inflammation, inflammatory diseases, sepsis, including septic shock, endotoxic shock, gram negative sepsis and toxic shock syndrome; autoimmune disease, including rheumatoid arthritis, juvenile arthritis, rheumatoid spondylitis, ankylosing spondylitis, Sjögren's syndrome, osteoarthritis and gouty arthritis, allergy, multiple sclerosis, autoimmune diabetes, autoimmune uveitis, psoriasis, pemphigoid and nephrotic syndrome; inflammatory conditions of the eye, including macular degeneration, uveitis, Behçet's disease; infectious disease, including fever and myalgias due to infection and cachexia secondary to infection; graft versus host disease; tumour growth or metastasis, hematologic malignancies; pulmonary disorders including asthma, adult respiratory distress syndrome, shock lung, chronic pulmonary inflammatory disease, pulmonary sarcoidosis, pulmonary fibrosis and silicosis; inflammatory bowel disorders including Crohn's disease and ulcerative colitis; cardiac disorders, congestive heart failure; vascular disorders including Wegener's disease, giant cell arteritis; inflammatory bone disorders, central nervous system disorders such as Alzheimer's disease; peripheral nervous system disorders such as sciatica, hepatitis, coagulation disturbances, burns, reperfusion injury, endometrosis, keloid formation and scar tissue formation.

In a particularly preferred embodiment, the disorder characterised by human TNF-α activity is age-related macular degeneration. TNF-α is implicated in stimulating VEGF production and promoting neovascularisation in the eye (Oh-H et al., 1999 Investigative Ophthalmology & Visual Science 40:1891-98), and therefore inhibitors of TNF-α activity, such as the domain antibody constructs described herein, would be useful for therapy of angiogenesis-related ocular disorders including age-related macular degeneration.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

In order that the nature of the present invention may be more clearly understood, preferred forms thereof will now be described with reference to the following non-limiting examples.

EXAMPLE 1

Materials and Methods

Isolation of New World Primate $V_L$ Genes

Marmoset (genus *Callithrix*, species unknown) and Owl monkey (*Aotus trivirgatus*) genomic DNA were obtained from the European Collection of Cell Cultures (ECACC), catalogue numbers 85011419 and 90110510 respectively. Marmoset DNA was derived from cell line B95-8 while Owl monkey DNA came from cell line OMK 637-69.

Degenerate primers based on human Vκ leader sequences and recombination signal sequences (RSS) were derived from Walter and Tomlinson, Antibody Engineering: A Practical Approach (1996). The primers used for amplification of germline Vκ DNA were as follows:

```
Primer VK1BL
AATCKCAGGTKCCAGATG          (SEQ ID No: 13)

Primer VK1BL35a
GTTYRGGTKKGTAACACT          (SEQ ID No: 14)

Primer VK1BL35b
ATGMCTTGTWACACTGTG          (SEQ ID No: 15)
```

PCR (30 cycles) was performed using Taq polymerase with either primer pair VK1BLxVK1BL35a or VK1BLxVK1BL35b. There was overlap between the sequences cloned and the two primer sets used.

Genomic PCR products were cloned into Invitrogen's TOPO TA cloning kit (Cat No K4500-01) and sequenced with M13 Forward and pUC Reverse primers. Sequence was confirmed in forward and reverse directions. In order to further confirm key sequences were not subject to PCR errors, the PCR and cloning process was repeated twice for marmoset sequences. Nucleotide (SEQ ID Nos:16-26 and SEQ ID Nos: 38-43) and amino acid (SEQ ID Nos:27-37 and SEQ ID Nos:44-49) are given in FIG. 3 (A-G). Marmoset sequences 1, 2 and 3 were confirmed. Sequences 4, 5, 6, 7 and 8 were seen only in the initial PCR. Sequences 9, 10 and 11 were seen only in the repeat (ie second) PCR and cloning.

Oligo Synthesis and Cloning into Acceptor Sequence

Four CDR sequences, namely YAATKLQS (SEQ ID No:1) from Owl monkey sequence 1 (SEQ ID No:44), YEASSLQS (SEQ ID No:2) from Owl monkey sequence 2 (SEQ ID No:45), YEASKLQS (SEQ ID No:3) from Marmoset sequence 1 (SEQ ID No:27), and YSASNLET (SEQ ID No:4) from Marmoset sequence 2 (SEQ ID No:28), were chosen from the amino acid sequences shown in FIG. 3 (A-G). Owl Monkey sequence 5, YYASSLQS (SEQ ID No:56) was found to be identical to GI6176295 an *Aotus nancymaae* (Ma's night monkey) cDNA sequence, all other sequences were unique.

The acceptor variable region (anti-TNF domain antibody) sequence in the expression vector (Domantis proprietary vector) was digested (25 μg) sequentially with KpnI and SanDI which excises the majority of FR2 as well as CDR2 as indicated on the restriction digest map, FIG. 4. The vector was then gel purified to remove the excised wild-type FR2 and CDR2 sequence.

Oligo annealing was performed by incubating oligo pairs (500 pmol, based on sequences shown in FIG. 3 (A-G)) at 95° C. for 5 minutes followed by 65° C. for 5 minutes and then allowed to reach room temperature slowly on a hot block. Overlaps were then filled in during a Klenow reaction in the presence of dNTPs. Molecular cloning of the synthetic double-stranded DNA (derived by oligo annealing and end filling) into the acceptor variable region sequence was achieved using standard methods.

Affinity Maturation

The marmoset CDR-grafted dAb Compound 145 (SEQ ID No:7) was affinity matured by constructing 14 separate libraries, each a diversification of the sequence of SEQ ID No:7 at a single amino acid residue. The selected residues are shown bolded below.

DIQMTQSPSSLSASVGDRVTITCRASQSIDSYLHWYQQKPGKAPKLLIYS

ASNLETGVPSRFSGSGSGTDFTLTISSLQPEDFATYYCQQVVWRPFTFGQ

GTKVEIKR

The selection was based upon residues in CDR1 and CDR3 that are known to be diversified in the mature human Ig repertoire, and framework residues that have been observed to produce functional proteins after mutagenesis in related dAbs. For each of the selected residues, complimentary forward and reverse PCR primer pairs were designed with NKK degeneracy, and two initial PCR reactions were performed each with a single mutagenic primer and flanking primer. After clean-up, the two PCR products were annealed and then amplified using flanking primers alone (splicing by overlap extension of PCR; Lowman H. L. & Clackson T. (eds), Phage Display: A practical approach, Oxford University Press, Oxford, UK). Clones were initially screened by ELISA using solid-phase TNF, and positive clones were sequenced. dAb protein was purified from the best clones and evaluated for potency in receptor binding assays and L929 cytotoxicity assays. Compounds 100 (SEQ ID No:9) and 123 (SEQ ID No:8) were found to have improved TNF-neutralization relative to the parent dAb, Compound 145 (SEQ ID No:7).

Combination of the affinity-enhancing substitutions of Compounds 100 and 123, yielded an anti-TNF dAb with further improved potency in the L929 cytotoxicity assay (Compound 196; SEQ ID No:10).

Cell Culture

CHOK1SV cells (Lonza Biologics, UK), a suspension variant of CHOK1, were maintained in logarithmic growth phase in CD CHO media supplemented with 6 mM L-glutamine (Invitrogen Cat Nos. 10743-029 and 25030-081). Cultures were incubated at 36.5° C., 10% $CO_2$ and shaking at 140 rpm. 24 hours before transfection cell number and viability was assessed by trypan blue exclusion (Sigma Cat No. T8154) on a haemocytometer. $8 \times 10^6$ viable cells were pelleted at 200×g for 5 minutes and resuspended in 8 ml of CM25 media (Lonza Biologics, UK) supplemented with 10% heat inactivated dialysed fetal calf serum (Invitrogen Cat No. 26400-044) and 6 mM L-glutamine. Cells were plated out at 500 μl per well in a 24 well plate and incubated at 36.5° C., 10% $CO_2$.

3 hours before transfection the media was replenished with a fresh aliquot of 500 μl CM25 media supplemented with 10% heat inactivated dialysed fetal calf serum and 6 mM L-Glutamine.

Expression Vectors

Gene sequences for Compound 112 (SEQ ID No:50) and Compound 170 (SEQ ID No:51) were optimized for mammalian cell expression and synthesized.

Compound 112

(SEQ ID No: 50)
GACATCCAGATGACCCAGAGCCCCAGCAGCCTGAGCGCCTCTGTGGGCGA

TAGAGTGACCATCACCTGCAGAGCCAGCCAGGCCATCGACAGCTACCTGC

ACTGGTATCAGCAGAAGCCTGGCAAGGCCCCTAAGCTGCTGATCTACAGC

GCCAGCAATCTGGAGACCGGCGTGCCTAGCAGATTCAGCGGCAGCGGCTC

CGGCACCGACTTCACCCTGACCATCAGCAGCCTGCTGCCTGAGGATTTCG

CCACCTACTACTGCCAGCAGGTGGTGTGGAGACCTTTCACCTTCGGCCAG

GGCACCAAGGTGGAGATCAAGCGGGTGGAGCCCAAGAGCTGCGATAAGAC

CCACACCTGCCCCCCCTGCCCTGCCCCCGAGCTGCTGGGCGGACCCAGCG

TGTTCCTGTTCCCCCCCAAGCCTAAGGACACCCTGATGATCAGCAGAACC

CCCGAGGTGACCTGCGTGGTGGTGGATGTGAGCCACGAGGACCCTGAGGT

GAAGTTCAACTGGTACGTGGACGGCGTGGAGGTGCACAATGCCAAGACCA

AGCCCAGGGAGGAGCAGTACAACAGCACCTACCGGGTGGTGTCCGTGCTG

ACCGTGCTGCACCAGGATTGGCTGAACGGCAAGGAGTACAAGTGCAAGGT

GTCCAACAAGGCCCTGCCTGCCCCTATCGAGAAAACCATCAGCAAGGCCA

AGGGCCAGCCCAGAGAGCCCCAGGTGTACACCCTGCCCCCTAGCAGAGAT

GAGCTGACCAAGAACCAGGTGTCCCTGACCTGCCTGGTGAAGGGCTTCTA

CCCCAGCGACATCGCCGTGGAGTGGGAGAGCAACGGCCAGCCCGAGAACA

ACTACAAGACCACCCCCCCTGTGCTGGACAGCGATGGCAGCTTCTTCCTG

TACAGCAAGCTGACCGTGGACAAGAGCAGATGGCAGCAGGGCAACGTGTT

CAGCTGCAGCGTGATGCACGAGGCCCTGCACAATCACTACACCCAGAAGA

GCCTGAGCCTGTCCCCTGGCAAG

Compound 170

(SEQ ID No: 51)
GACATCCAGATGACCCAGAGCCCCAGCAGCCTGAGCGCCTCTGTGGGCGA

TAGAGTGACCATCACCTGCAGAGCCAGCCAGGCCATCGACAGCTACCTGC

ACTGGTATCAGCAGAAGCCTGGCAAGGCCCCTAAGCTGCTGATCTACAGC

GCCAGCAATCTGGAGACCGGCGTGCCTAGCAGATTCAGCGGCAGCGGCTC

CGGCACCGACTTCACCCTGACCATCAGCAGCCTGCTGCCTGAGGATTTCG

CCACCTACTACTGCCAGCAGGTGGTGTGGAGACCTTTCACCTTCGGCCAG

GGCACCAAGGTGGAGATCAAGCGGGTGGAGCCCAAGAGCAGCGATAAGAC

CCACACCTGCCCCCCCTGCCCTGCCCCCGAGCTGCTGGGCGGACCCAGCG

```
                                    -continued
TGTTCCTGTTCCCCCCAAGCCTAAGGACACCCTGATGATCAGCAGAACC

CCCGAGGTGACCTGCGTGGTGGTGGATGTGAGCCACGAGGACCCTGAGGT

GAAGTTCAACTGGTACGTGGACGGCGTGGAGGTGCACAATGCCAAGACCA

AGCCCAGGGAGGAGCAGTACAACAGCACCTACCGGGTGGTGTCCGTGCTG

ACCGTGCTGCACCAGGATTGGCTGAACGGCAAGGAGTACAAGTGCAAGGT

GTCCAACAAGGCCCTGCCTGCCCCTATCGAGAAAACCATCAGCAAGGCCA

AGGGCCAGCCCAGAGAGCCCCAGGTGTACACCCTGCCCCCTAGCAGAGAT

GAGCTGACCAAGAACCAGGTGTCCCTGACCTGCCTGGTGAAGGGCTTCTA

CCCCAGCGACATCGCCGTGGAGTGGGAGAGCAACGGCCAGCCCGAGAACA

ACTACAAGACCACCCCCCCTGTGCTGGACAGCGATGGCAGCTTCTTCCTG

TACAGCAAGCTGACCGTGGACAAGAGCAGATGGCAGCAGGGCAACGTGTT

CAGCTGCAGCGTGATGCACGAGGCCCTGCACAATCACTACACCCAGAAGA

GCCTGAGCCTGTCCCCTGGCAAG
```

Each sequence was flanked at the 5' end with a Hind III site, a Kozak sequence (GCCACC; SEQ ID No:57) and a human IgG kappa leader sequence (amino acid sequence MSVPTQVLGLLLLWLTDARC; SEQ ID No:58). At the 3' end two stop codons and an EcoR I site were added to each sequence. Following synthesis genes were provided cloned into a pCRScript vector (Stratagene) and were released by Hind III/EcoR I digestion in the appropriate restriction enzyme buffer (Roche Diagnostics Cat Nos. 10656313001, 10703737001 and 11417967001 respectively). The GS expression vector pEE12.4 (Lonza Biologics, UK) was similarly digested and dephosphorylated using calf intestinal alkaline phosphatase Roche Diagnostics Cat No. 10713023001). Each gene was ligated into the prepared pEE12.4 backbone using the LigaFast Rapid DNA Ligation System from Promega (Cat No. M8221). Ligations were then transformed into One Shot Top 10 chemically competent cells (Invtrogen Cat No. C4040-03) and positive colonies identified by standard techniques. Large quantities of the resulting vectors (pEE12.4-PNO621 and pEE12.4-PNO521-S114C) were prepared by midiprep of overnight cultures using QIAfilter midiprep columns (QIAgen Cat No. 12243). Vectors were prepared for transfection by precipitating 20 µg in 100% ethanol with ⅒ volume of 3 M sodium acetate (pH 5.2) (Sigma Cat Nos. E7023 and S2889 respectively). Following a wash in 70% ethanol, vectors were resuspended in 40 µl of T.E. pH 8.0 (Sigma Cat No. T9285) at a working concentration of 0.5 µg/µl.

Transfection

For each transfection 2 µl of Lipofectamine 2000 was added to 50 µl of Optimem I media (Invitrogen Cat Nos. 11668-027 and 31985-062) in a well of a 96 well plate. In a second well 1.6 µl of the expression vector (0.8 µg) was added to 50 µl of Optimem I media. Following a 5 minute room temperature incubation the contents of the two wells were mixed together and left for a further 20 minute incubation. Following this second incubation the whole transfection mixture was added to a well in the 24 well plate containing the CHOK1SV cells. Cells were incubated for at least 72 hours and supernatants harvested. Supernatants were centrifuged at 4,000×g for 5 minutes to pellet cell debris and were stored at −20° C. until expression of Compound 112 (SEQ ID No:59) and Compound 170 (SEQ ID No:11) was assayed by TNF ELISA.

```
Compound 112
                                              (SEQ ID No: 59)
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKRVEPKSCDKTHTCPPCPAPELLGGPSVFLFPPKPKDTLMISRT

PEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFL

YSKLTVDKSRWQQGNVFSCSVMHEALHNHYTQKSLSLSPGK
```

TNF Elisa

Microtitre plates (e.g. Sarstedt 82.9923-148) were coated with a 1 µg/mL solution of human recombinant TNF-α (Peprotech Cat #300-01A) in carbonate/bicarbonate coating buffer pH 9.6, 100 µL/well. After overnight incubation at 4° C., plates were washed 3 times with PBS (0.01 M, pH 7.2) with 0.05% Tween 20, and 3 times with PBS. 200 µL blocking buffer (PBS with 1% BSA {bovine serum albumin, Sigma Cat # A-9647}) was added per well and incubated at 25° C. for 1 hour. Plates were washed, as above, and 100 µL volumes of sample or Compound 170 standards diluted in antibody diluent (PBS with 1% BSA and 0.05% Tween 20) were added per well. After 1 hour incubation at 25° C., plates were washed, as above, and 100 µL volumes of secondary antibody (peroxidase-conjugated goat anti-human immunoglobulins, Zymed, Cat #81-7120) at 1:1000 dilution in antibody diluent were added per well. Plates were washed and 100 µL volumes of ABTS substrate (2,2'-Azino-bis(3-Ethylbenz-Thiazoline-6-Sulfonic acid) diammonium salt, Sigma Cat #A-1888, 0.5 mg/mL in citrate buffer pH 4.4, with 0.03% $H_2O_2$) were added per well. Substrate was developed for 30 minutes at room temperature and absorbance read at 405 nm (reference 620 nm). Sample concentrations were determined relative to the standard curve and were expressed relative to the mean concentration of Compound 112 expressed.

Results

Inclusion of Truncated $C_H1$

Inclusion of the truncated CH1 in the domain antibody construct results in a junction between the variable domain and hinge with higher homology to a conventional IgG1 CH1-hinge junction (91.7%) than a junction lacking the truncated CH1 (83.3%; calculated using Align X on Vector NTI (Invitrogen) with a gap opening penalty of 1). Enhanced homology is likely to translate to increased resemblance to conventional immunoglobulin peptide sequences to which human patients should be immunologically tolerant, thereby reducing immunogenic potential.

Sequences:

| | |
|---|---|
| Compound 170 variable region-truncated CH1-hinge junction: | TKVEIKRVEPKS (SEQ ID NO: 65) |
| IgG1 CH1-hinge junction (NCBI accession AAG00909): | TKVDKRVEPKS (SEQ ID NO: 66) |
| Compound 170 variable region-hinge junction (truncated CH1 absent): | TKVEIKREPKS (SEQ ID NO: 67) |

CH1 sequence is bolded as indicated.

CH1 domain (SEQ ID No:60) obtained from NCBI protein database (http://www.ncbi.nlm.nih.gov) AAG00909:

```
  1 STKGPSVFPL APSSKSTSGG TAALGCLVKD YFPEPVTVSW NSGALTSGVH TFPAVLQSSG

61 LYSLSSVVTV PSSSLGTQTY ICNVNHKPSN TKVDKRVEPK SCDKTHTCPP CPAPELLGGP

121 SVFLFPPKPK DTLMISRTPE VTCVVVDVSH EDPEVKFNWY VDGVEVHNAK TKPREEQYNS

181 TYRVVSVLTV LHQDWLNGKE YKCKVSNKAL PAPIEKTISK AKGQPREPQV YTLPPSREEM

241 TKNQVSLTCL VKGFYPSDIA VEWESNGQPE NNYKTTPPVL DSDGSFFLYS KLTVDKSRWQ

301 QGNVFSCSVM HEALHNHYTQ KSLSLSPGK
```

CH1-hinge junction is indicated in underline.

Neutralization of TNF-α-Induced Cytotoxicity

Figure 6:
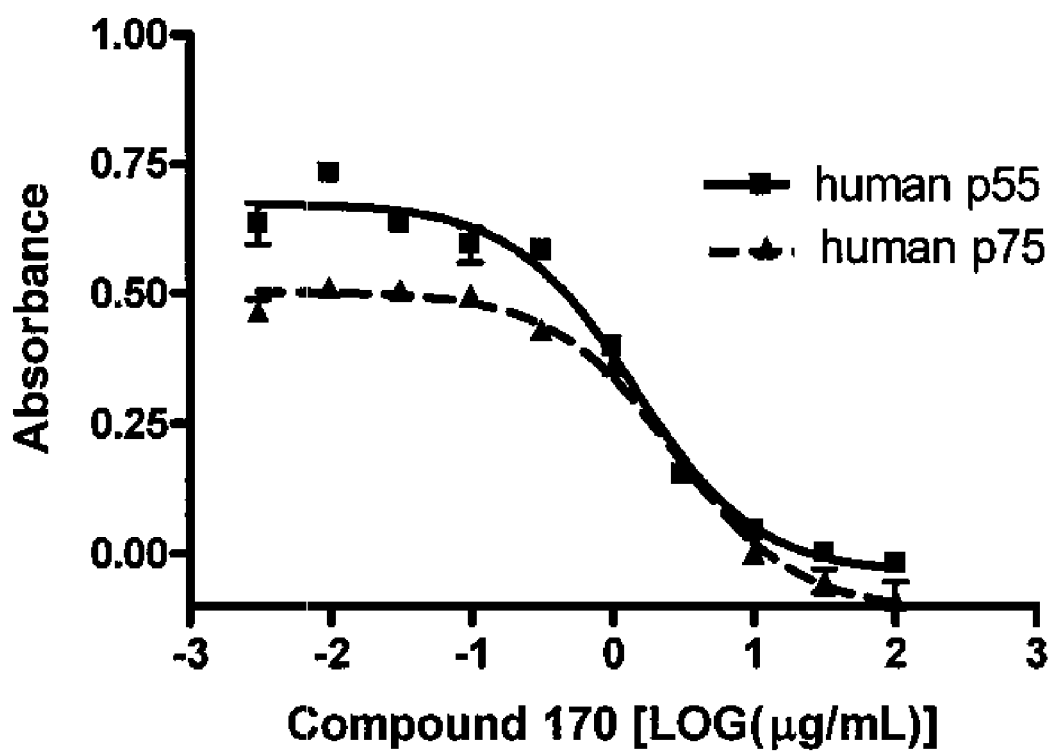
FIG. 6 shows that Compound 170 (SEQ ID No:11) prevents the interaction of TNF-α with the human p55 or p75 TNF receptors.

The ability of the domain antibody construct Compound 170 (SEQ ID No:11) to neutralize TNF-α-mediated cytotoxicity was assessed using a murine L929 cell viability assay. Serial dilutions of Compound 170 in RPMI medium with 10% foetal bovine serum (RPMI-FBS) were prepared in 50 μL volumes in flat bottomed 96 well plates. To each of these wells was added 50 μL recombinant human TNF-α (Strathmann Biotec, Hamburg, Germany) at a concentration of 360 pg/mL, followed by $2.5 \times 10^4$ L929 cells in 50 μL and 25 μL Actinomycin D at 40 μg/mL, all prepared in RPMI-FBS. Controls included wells with no TNF (for determination of 100% viability), no cells (0% viability) and a TNF-α standard curve ranging from 2 pg/mL to 4200 pg/mL. Culture plates were incubated in a 5% $CO_2$ atmosphere at 37° C. for 20 hours, then for a further 3 hours after the addition of 25 μL 3-(4,5-dimethylthiazol-2yl)-5-(3-carboxymethoxyphenyl)-2-(4-sulfophenyl)-2H-tetrazolium (MTS)/phenazine ethosulfate (PES) (Promega CellTiter 96 AQ$_{ueous}$ One, Madison USA). Absorbance at 492 nm was determined against a reference wavelength of 630 nm and viability curves were plotted using average values calculated from triplicate test wells. The TNF-α-neutralizing ability of Compound 170 is indicated by increasing cell viability with increasing concentrations of Compound 170 (FIG. 6).

Neutralization of TNF-α Binding to Human p55 and p75 TNF Receptors

The ability of the domain antibody construct Compound 170 (SEQ ID No:11) to inhibit binding of TNF-α to human p55 and p75 TNF receptors was evaluated by receptor binding assays. Human p55 (RnD systems, Cat No: 372-RI) or p75 (RnD systems, Cat No: 762-R2) was coated onto Maxisorb plates (Nunc) at 0.1 μg/mL in carbonate coating buffer pH 9.2 by overnight incubation at 4° C. Serial half-log dilutions of Compound 170 ranging from 100 μg/mL down to 3.15 ng/mL (and a no Compound 170 'blank' control) were prepared in antibody diluent (PBS pH 7.2, 0.05% Tween-20, 1% BSA) and were mixed with an equal volume of 60 ng/mL human TNF-α in antibody diluent. A blank containing no PN0621 and no TNF-α was also prepared to measure background binding. All mixtures were allowed to incubate for exactly 1 hour at room temperature with gentle agitation. During this incubation the coated plates were washed 3 times with PBS, 0.05% Tween-20 and then 3 times with PBS. The plates were then blocked with 200 μl/well of PBS, 1% BSA for 45 minutes at room temperature. Following washing of the plate, 100 μl of the Compound 170/TNF-α mixtures were added to triplicate wells for each concentration of Compound 170 tested along with addition of all the controls. The plate was then incubated at room temperature for 1 hour. Following washing of the plate, a biotinylated anti-human TNF-α antibody (RnD Systems, Cat No: BAF210) was added at 0.6 μg/mL in antibody diluent to each well and incubated for 1 hour at room temperature. Following washing a Streptavidin-HRP conjugate (Zymed, Cat No: 43-4323) was added at 1:2000 in antibody diluent and incubated at room temperature for 45 mins. Visualization was performed using TMB substrate (Invitrogen, Cat No: 00-2023) stopped with 1 M HCl after 4 minutes. Absorbance readings were then measured at 450 nm using a reference of 620 nm. Analysis was performed by calculating the average absorbance of the triplicates. The average of the non-specific binding (no TNF-α) was subtracted from each absorbance value.

Figure 7:
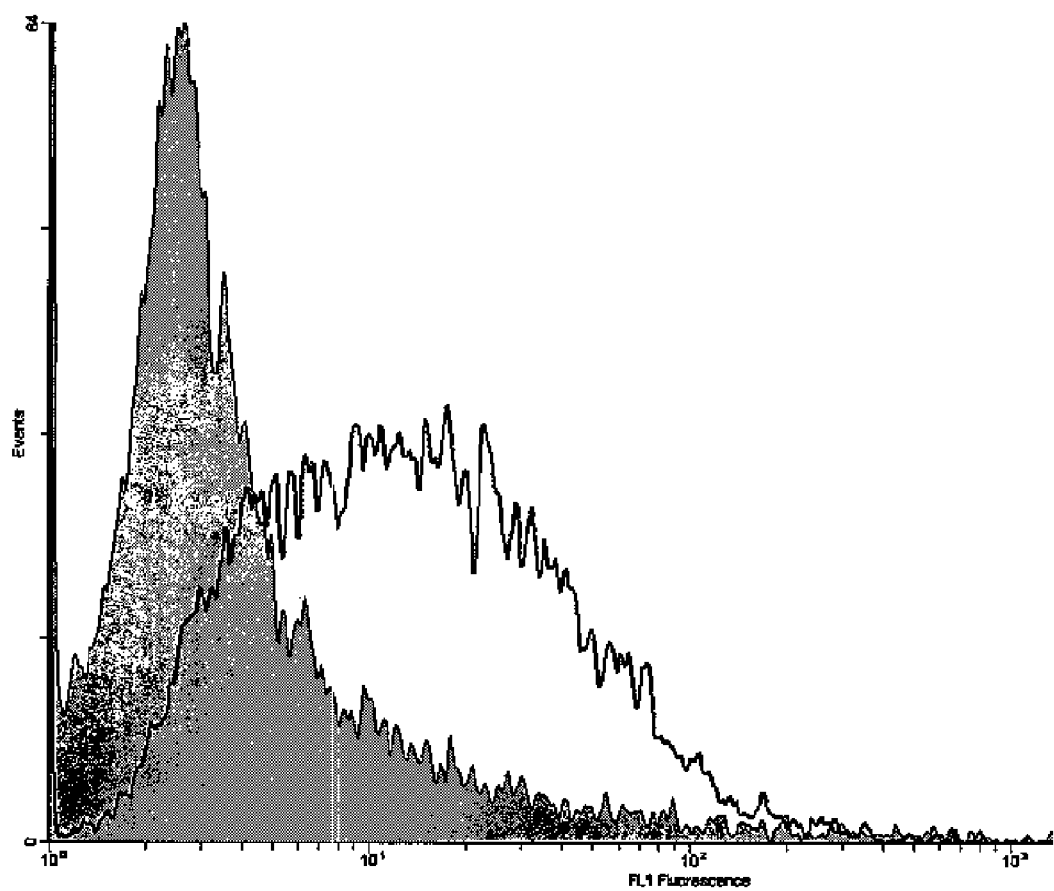
FIG. 7 shows Compound 170 (SEQ ID No:11) staining of transmembrane TNF-α-expressing NS0 27D4 cells (solid black line) shows higher fluorescence intensity than irrelevant specificity isotype-matched control (grey fill).

The results are indicated in FIG. 7 and show that Compound 170 prevents the interaction of TNF-α with the human p55 or p75 TNF receptors.

Binding of Cell-Bound TNF-α

Analysis of binding to cell-bound (transmembrane) TNF-α was performed using an NS0 cell line, 27D4, stably transfected with a gene encoding human TNF-α protein lacking a TACE cleavage site, such that TNF-α remains cell membrane-associated because it cannot be cleaved. A similar cell line based on another murine myeloma (SP2/0) has been described (Scallon et al., (1995) Cytokine 7 251-259).

Flow cytometry analysis was performed on $5 \times 10^5$ viable 27D4 cells per sample with all steps performed at 4° C. or on ice. Cell pellets were resuspended with test (Compound 170; SEQ ID No:11) or irrelevant-specificity isotype-matched control (Sigma, Cat No: I5154) at 100 μg/ml in PBS containing 2% FBS, and incubated on ice for 1 hour. Two cell wash cycles were performed, each comprising, centrifugation for 10 minutes at 1000×g and resuspension of the cell pellet in PBS/2% FBS. Following another centrifugation step the cell pellet was resuspended in 100 μl secondary antibody conjugate (Anti-human Fc FITC conjugate, Sigma, Cat No: F9512) and incubated for 30 mins. The samples were then washed twice as described above and cell pellets resuspended in 500 μl PBS/2% FBS with 5 μg/mL propidium iodide (Sigma, Cat no: P4864). Fluorescent staining of cells was analysed on a Beckman Coulter Cell Lab Quanta flow cytometer and data was processed using WinMDI.

Figure 8:
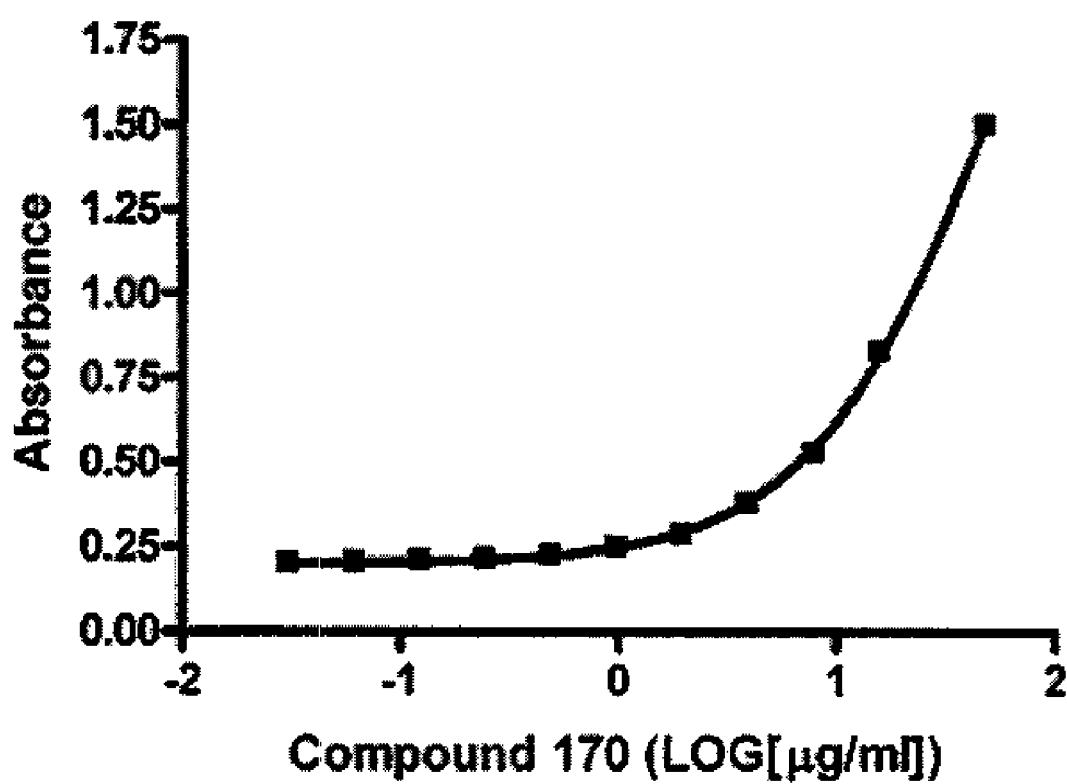
FIG. 8 shows Compound 170 (SEQ ID No:11) produced in a bacterial expression system retained binding to TNF-α in an ELISA.

The results are indicated in FIG. 8, and show that Compound 170 staining of transmembrane TNF-α-expressing NS0 27D4 cells (solid black line) shows higher fluorescence intensity than irrelevant specificity isotype-matched control (grey fill).

Creation of High Compound 170-Expressing Cell Lines

Stable cell lines of CHOK1SV expressing Compound 170 (SEQ ID No:11) were created using the expression vector described in the Materials and Methods. Briefly $1 \times 10^7$ cells in logarithmic growth phase were electroporated in glutamine-free CDCHO protein-free media in the presence of 40 μg of linearised plasmid DNA. 24 hours post-transfection a selective pressure of 50 μM methionine sulphoximine (Sigma) was applied and resistant cells were allowed to form colonies in 96 well plates. When approaching confluence, single colonies were transferred to 24 well plates, T25 and then T75 flasks. Once over confluent in T75 flasks cell lines were progressed to culture in E125 Erlenmeyer flasks and adapted to suspension growth over 6 subcultures. Once adapted to suspension growth cell lines were cryopreserved in a freeze mix of 92.5% CDCHO media:7.5% DMSO.

Whilst cell lines were being expanded through the different well and flask sizes, a number of productivity assessments were performed in parallel to the progress of the cell lines to the next stage. Thus at the 24 well plate and E125 Erlenmeyer flask stages productivity assessments were performed. In each case cells were allowed to grow for 14 days and supernatants evaluated by the TNF ELISA method described in Example 1 for levels of Compound 170. Cell lines were ranked on the productivity and the highest 10 were selected for evaluation in a proprietary fed-batch productivity assessment at Lonza Biologics. Productivities obtained were between 700 mg/L and 3371 mg/L. A lead cell line with a productivity of 2724 mg/L was selected for evaluation in 10 L laboratory scale fermenters.

Four separate 10 L laboratory scale fermenters were run over 15 days with the lead cell line and a proprietary generic fed batch process based on the protein-free CDCHO media. The resulting mean productivity of the 4 fermentations was 4851 mg/L with the highest productivity being 4925 mg/L (the highest reported level of productivity previously reported by Lonza Biologics for a non clonal cell line in a 15 day fermentation is 3560 mg/L). The 10 L laboratory-scale fermenters used were designed to mimic the fermentation conditions found in larger scale fermenters up to 2000 L, hence the lead cell line is expected to be suitable for commercial scale manufacture. Indeed similar expression levels were observed in a 200 L fermenter.

Figure 11:
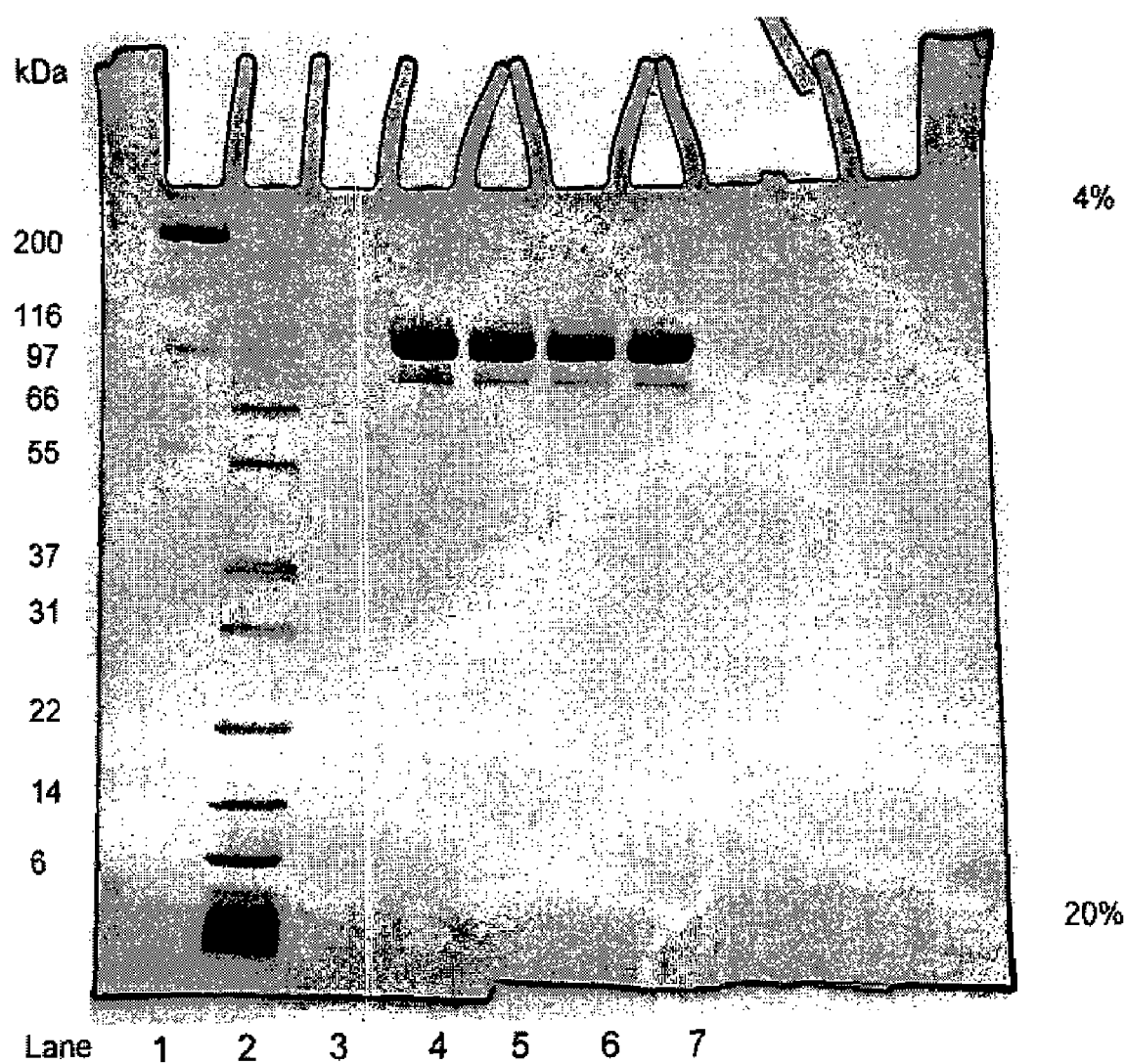
FIG. 11 shows non-reducing SDS PAGE analysis of Protein A purified Compound 170 (SEQ ID No:11) from 4×10 L fermentations of the lead cell line; lane 1=inter-assay control; lane 2=molecular weight markers; lane 3=blank; lane 4=Protein A purified Compound 170 (SEQ ID No: 11) in 10 L fermentation ID (run 1); lane 5=Protein A purified Compound 170 in 10 L fermentation ID (run 2); lane 6=Protein A purified Compound 170 in 10 L fermentation ID (run 3); lane 7=Protein A purified Compound 170 in 10 L fermentation ID (run 4).
Figure 12:
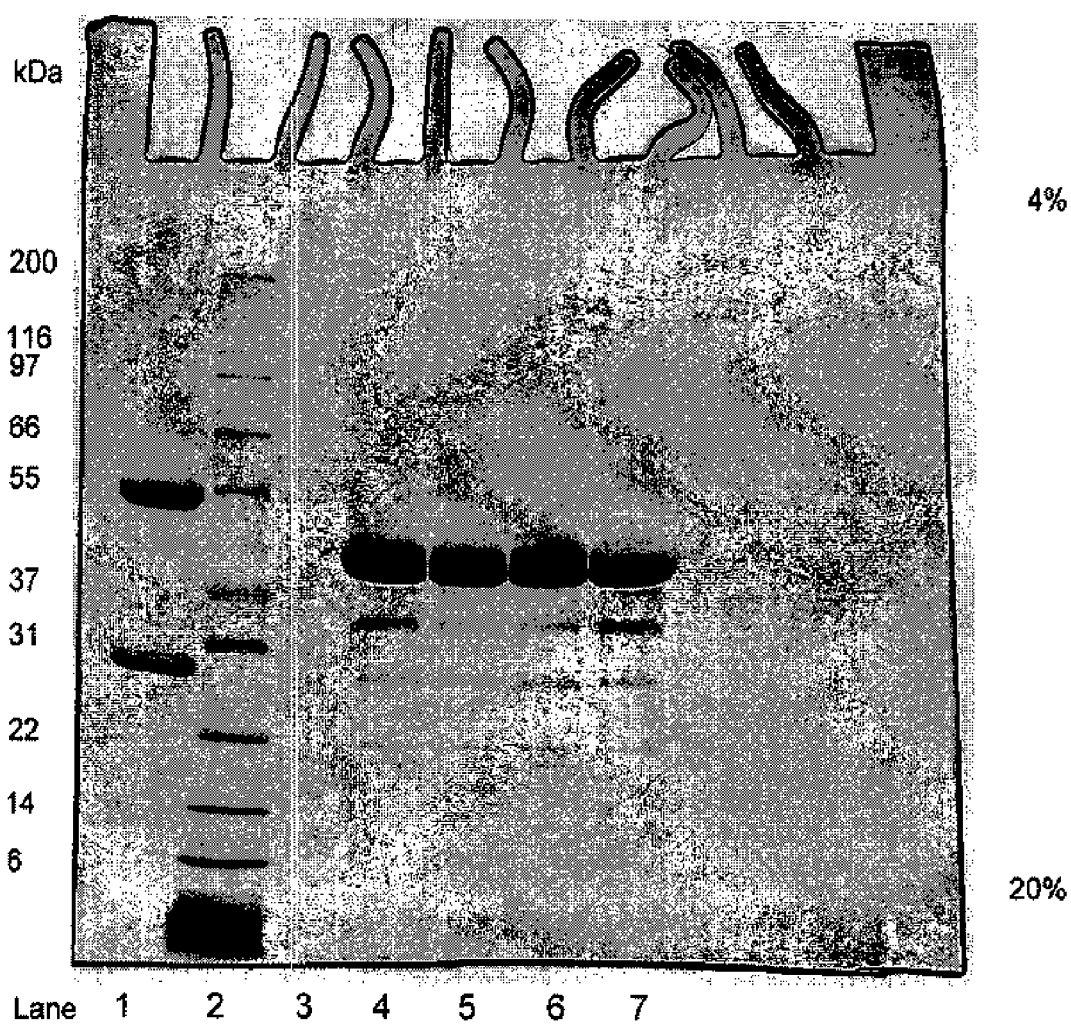
FIG. 12 shows reducing SDS PAGE analysis of Protein A purified Compound 170 (SEQ ID No:11) from 4×10 L fermentations of the lead cell line; lane 1=inter-assay control; lane 2=molecular weight markers; lane 3=blank; lane 4=Protein A purified Compound 170 (SEQ ID No:11) in 10 L fermentation ID (run 1); lane 5=Protein A purified Compound 170 in 10 L fermentation ID (run 2); lane 6=Protein A purified Compound 170 in 10 L fermentation ID (run 3); lane 7=Protein A purified Compound 170 in 10 L fermentation ID (run 4).

Product harvested from the 4×10 L fermentations of the lead cell line expressing Compound 170 (SEQ ID No:11) was purified by Protein A affinity chromatography and analysed by SDS PAGE under both reducing and non-reducing conditions. As shown in FIG. 11, Compound 170 is expressed as a monomer of approximately 90 kDa. This monomer is composed of 2 subunits of approximately 40 kDa which are apparent in FIG. 12 when the SDS PAGE is run under reducing conditions. Since SDS PAGE is not suitable for exact sizing of proteins further analysis of the Compound 170 monomer has been performed. ESI-MS (electrospray ionisation mass spectrometry) has sized the Compound 170 monomer at 78.739 kDa. This is in agreement with the predicted molecular weight of 2 subunits (2×38.058=76.116 kDa) each of which also carry a bi-antennary core fucosylated glycan sugar structure.

Long Serum Half-Life in Non-Human Primates

Compound 170 (SEQ ID No:11) was administered subcutaneously to cynomolgus monkeys at doses of 0.5, 5 and 50 mg/kg, and blood samples were taken at 0.5, 1, 2, 6 and 24 hours then at 1 day, 2, 4, 7, 10 and 14 days. Analysis of these samples for quantitation of Compound 170 levels was performed using the anti-TNF ELISA method described in Example 1. Elimination half-life was determined by analysis of the levels of Compound 170 in these samples. At 0.5 mg/Kg an elimination half-life of 110.5±13.9 hours was calculated. At 5 mg/Kg and 50 mg/Kg elimination half-lives of 110.9±10.4 and 103.5±11.5 hours were calculated.

When Compound 170 was administered by intravenous route at 50 mg/Kg blood samples were taken at 10, 30 and 60 minutes, 4 and 24 hours, 2, 4, 7, 10 and 14 days. Analysis of these samples for quantitation of Compound 170 levels was performed using the anti-TNF ELISA method described in Example 1. Elimination half-life was determined by analysis of the levels of Compound 170 in these samples. Following 50 mg/Kg intravenous administration an elimination half-life of 109.6±10.7 hours was calculated.

Favorable Safety Profile

Compound 170 (SEQ ID No:11) manufactured to GMP standards was evaluated in animal safety and toxicology studies.

Single Dose Safety

Different monkeys administered single doses of Compound 170 at 0.5, 5 and 50 mg/kg by subcutaneous or intravenous route of administration showed no effects related to their treatment with Compound 170. In these studies microscopic examination of a range of organs was undertaken and no effects were observed.

Escalating Dose and Repeat Dose Safety

Starting with a dose of 0.5 mg/kg given either subcutaneously or intravenously escalating doses up to 50 mg/kg were administered to cynomolgus monkeys every 7 days. Animals were assessed for a wide range of physiological and behavioural parameters including haematology, clinical chemistry, body and organ weight and macroscopic inspection of organs following necropsy. Throughout these studies no adverse reactions to the treatment with Compound 170 were reported. Following the conclusion of the dose escalation phase of studies those animals which received the escalating dose subcutaneously were administered with a further 4 doses of 50 mg/kg over a further 4 week period. Again no effects, across the wide range of parameters, related to the treatment with Compound 170 were observed.

Cardiovascular Safety

The cardiovascular safety of Compound 170 at 50 mg/kg was evaluated in cynomolgus monkeys fitted with radio-telemetry monitors. These monitors report a range of respiratory and cardiovascular parameters directly from the conscious monkeys. Following dosing with Compound 170 no adverse treatment-related clinical observations were reported.

Bacterial Expression

Compound 170 (SEQ ID No: 11) in preceding examples was produced in mammalian expression systems. Functional Compound 170 was also produced using a bacterial expression system.

The amino acid sequence for Compound 170 minus the signal sequence was back-translated and optimized by GeneOptimizer™ for *E. coli* expression and synthesized de novo at GeneArt GmbH. The synthesized gene was subcloned into the pBAD gIII/His-tagged expression vector (Invitrogen) via NcoI and HindIII restriction sites (Roche) generating a vector ready for bacterial expression. TOP10 cells (Invitrogen) were transformed with the vector by the heat shock method and glycerol stocks of single colonies generated. Induction conditions were 0.002% arabinose (Sigma; final concentration) and 4 hr induction period. Compound 170 protein samples were generated using the osmotic shock method as detailed in the pBAD bacterial expression system manual (Invitrogen). The BCA assay (Pierce) was used to determine the total protein concentration of the samples. Bacterially-expressed Compound 170 was assayed for binding to TNF-α in an ELISA as described in Example 1.

Figure 9A:
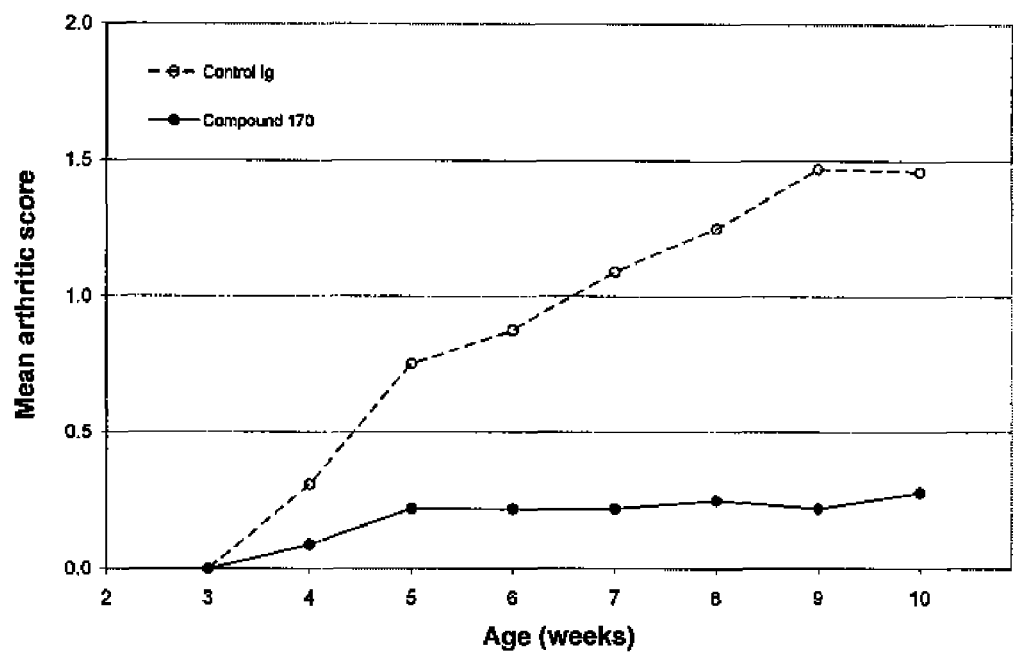
FIG. 9 shows the efficacy of Compound 170 (SEQ ID No:11) in a TNF-mediated murine arthritis model relative to specificity control human IgG$_1$. At weekly intervals mice were scored (arthritic score), (A), and weighed, (B).
Figure 9B:
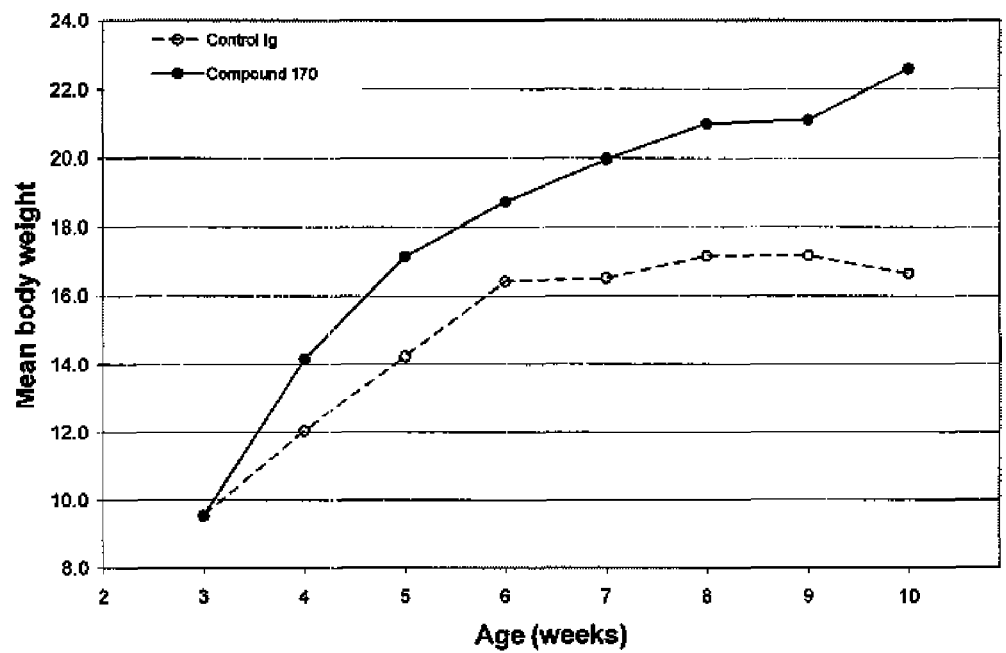

FIG. 9 shows that Compound 170 produced in a bacterial system retained binding to TNF-α in an ELISA assay.

The DNA sequence for bacterial expression of Compound 170 is as follows:

(SEQ ID No: 61)
ATGGCGAGCACCGATATTCAGATGACCCAGAGCCCGAGCAGCCTGAGCGC

GAGCGTGGGTGATCGTGTGACCATTACCTGCCGTGCGAGCCAGGCGATTG

ATAGCTATCTGCATTGGTATCAGCAGAAACCGGGCAAAGCGCCGAAACTG

CTGATTTATAGCGCGAGCAACCTGGAAACCGGCGTGCCGAGCCGTTTTAG

CGGCAGCGGTAGCGGCACCGATTTTACCCTGACCATTAGCAGCCTGCTGC

CGGAAGATTTTGCGACCTATTATTGCCAGCAGGTGGTGTGGCGTCCGTTT

ACCTTTGGCCAGGGCACCAAAGTGGAAATTAAACGCGTGGAACCGAAAAG

CAGCGATAAAACCCACACGTGCCCGCCGTGTCCGGCGCCGGAACTGCTGG

GTGGCCCGAGCGTGTTTCTGTTTCCGCCGAAACCGAAAGATACCCTGATG

ATTAGCCGTACCCCGGAAGTGACCTGCGTGGTGGTGGATGTGAGCCATGA

AGATCCGGAAGTGAAATTCAACTGGTATGTGGATGGCGTGGAAGTGCATA

ACGCGAAAACCAAACCGCGTGAAGAACAGTATAACAGCACCTATCGTGTG

GTGAGCGTGCTGACCGTGCTGCATCAGGATTGGCTGAACGGCAAAGAATA

CAAATGCAAAGTGTCTAACAAAGCGCTGCCGGCGCCGATTGAAAAAACCA

TCAGCAAAGCGAAAGGCCAGCCGCGTGAACCGCAGGTGTATACCCTGCCG

CCGAGCCGTGATGAACTGACCAAAAACCAGGTGAGCCTGACCTGCCTGGT

GAAAGGCTTTTATCCGAGCGATATTGCGGTGGAATGGGAAAGCAACGGCC

AGCCGGAAAACAACTATAAAACCACCCCGCCGGTGCTGGATAGCGATGGC

AGCTTTTTCCTGTATAGCAAACTGACCGTGGATAAAAGCCGTTGGCAGCA

GGGCAACGTGTTTAGCTGCAGCGTGATGCATGAAGCGCTGCATAACCATT

ATACCCAGAAAAGCCTGAGCCTGAGCCCGGGTAAAGCGGCGGCG

The amino acid sequence encoded by SEQ ID No:61 is as follows:

(SEQ ID NO: 62)
MASTDIQMTQSPSSLSASVGDRVTITCRASQAIDSYLHWYQQKPGKAPKL

LIYSASNLETGVPSRFSGSGSGTDFTLTISSLLPEDFATYYCQQVVWRPF

TFGQGTKVEIKRVEPKSSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGKAAAVD

HHHHHH

In Vivo Efficacy of Compound 170 in a Human TNF-Mediated Marine Arthritis Model

Figure 10:
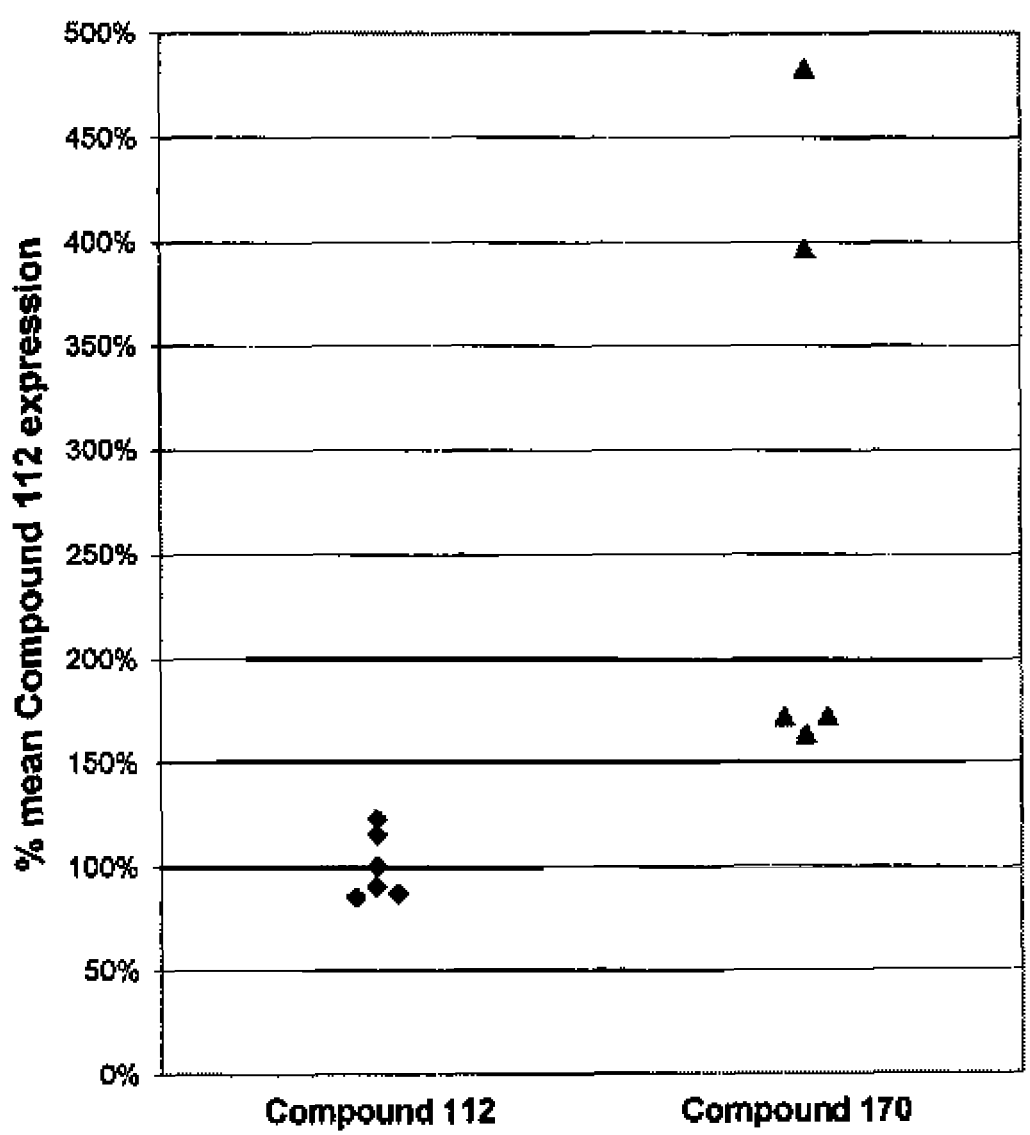
FIG. 10 shows the effect on protein expression of Compound 112 (SEQ ID No:59) and Compound 170 (SEQ ID No:11).

The human TNF transgenic mouse line, Tg197, shows deregulated TNF expression and develops chronic inflammatory polyarthritis (Keffer, J. et. al. (1991) Transgenic mice expressing human tumor necrosis factor: a predictive genetic model of arthritis. EMBO Journal 10:4025-31). Administration of Compound 170 (SEQ ID No:11) prevented the development of arthritis and associated weight loss in these mice (FIGS. 10A & B). Groups of 8 heterozygous Tg197 (each containing 4 males and 4 females) were treated with twice weekly intraperitoneal injections of Compound 170 and irrelevant specificity control human IgG$_1$ (palivizumab {Synagis®}, MedImmune/Abbott) in PBS, both at 10 mg/kg. Treatment commenced when mice were 3 weeks of age. At weekly intervals, mice were weighed and scored (arthritic score) based on macroscopic ankle morphology (swelling, distortion and degree of movement).

Substitution of Cys at Position 114 in Compound 112 Results in Increased Protein Expression Compound 112 (SEQ ID No: 59) is a modification of Compound 170 (SEQ ID No:11) which contains a cysteine residue at position 114 instead of a serine residue which is present in this position in Compound 170. The effect of substituting cysteine 114 for serine on protein expression was evaluated by comparison with Compound 170. Multiple cultures of host cells transfected with gene constructs for Compound 112 and 170 were assayed for protein expression by ELISA with solid phase TNF as set out in Materials and Methods. The results are set out in FIG. 11.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A domain antibody construct which binds to human TNF-α, wherein the amino acid sequence of the domain antibody construct is identical to the sequence set forth in SEQ ID No:11.

2. A dimeric domain antibody construct which binds to human TNF-α, wherein the dimeric domain antibody construct consists of two domain antibody constructs according to claim 1 and which is homodimer.

3. A pharmaceutical composition comprising a therapeutically effective amount of a domain antibody construct according to claim 1, together with a pharmaceutically acceptable carrier or diluent.

4. A pharmaceutical composition comprising a therapeutically effective amount of a dimeric domain antibody construct according to claim 2, together with a pharmaceutically acceptable carrier or diluent.

* * * * *

SEQUENCE LISTING

<160> NUMBER OF SEQ ID NOS: 68

<210> SEQ ID NO 1
<211> LENGTH: 8
<212> TYPE: PRT
<213> ORGANISM: Aotus trivirgatus

<400> SEQUENCE: 1

Tyr Ala Ala Thr Lys Leu Gln Ser
1               5

<210> SEQ ID NO 2
<211> LENGTH: 8

-continued

```
<212> TYPE: PRT
<213> ORGANISM: Aotus trivirgatus

<400> SEQUENCE: 2

Tyr Glu Ala Ser Ser Leu Gln Ser
 1               5

<210> SEQ ID NO 3
<211> LENGTH: 8
<212> TYPE: PRT
<213> ORGANISM: Callithrix, species unknown

<400> SEQUENCE: 3

Tyr Glu Ala Ser Lys Leu Gln Ser
 1               5

<210> SEQ ID NO 4
<211> LENGTH: 8
<212> TYPE: PRT
<213> ORGANISM: Callithrix, species unknown

<400> SEQUENCE: 4

Tyr Ser Ala Ser Asn Leu Glu Thr
 1               5

<210> SEQ ID NO 5
<211> LENGTH: 108
<212> TYPE: PRT
<213> ORGANISM: Artificial Sequence
<220> FEATURE:
<223> OTHER INFORMATION: Synthesized construct

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
             20                  25                  30

Leu His Trp Tyr Gln Gln Lys Pro Gly Lys Ala Pro Lys Leu Leu Ile
         35                  40                  45

Tyr Ser Ala Ser Glu Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg
            100                 105

<210> SEQ ID NO 6
<211> LENGTH: 324
<212> TYPE: DNA
<213> ORGANISM: Artificial Sequence
<220> FEATURE:
<223> OTHER INFORMATION: Synthesized construct

<400> SEQUENCE: 6
gacatccaga tgacccagtc tccatcctct ctgtctgcat ctgtaggaga ccgtgtcacc    60
atcacttgcc gggcaagtca gagcattgat agttatttac attggtacca gcagaaacca   120
gggaaagccc ctaagctcct gatctatagt gcatccgagt tgcaaagtgg ggtcccatca   180
cgtttcagtg gcagtggatc tgggacagat ttcactctca ccatcagcag tctgcaacct   240
```

```
gaagattttg ctacgtacta ctgtcaacag gttgtgtggc gtcctttac gttcggccaa      300 gggaccaagg tggaaatcaa acgg                                             324
```

<210> SEQ ID NO 7
<211> LENGTH: 108
<212> TYPE: PRT
<213> ORGANISM: Artificial Sequence
<220> FEATURE:
<223> OTHER INFORMATION: Synthesized construct

<400> SEQUENCE: 7

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

<210> SEQ ID NO 8
<211> LENGTH: 108
<212> TYPE: PRT
<213> ORGANISM: Artificial Sequence
<220> FEATURE:
<223> OTHER INFORMATION: Synthesized construct

<400> SEQUENCE: 8

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

<210> SEQ ID NO 9
<211> LENGTH: 108
<212> TYPE: PRT
<213> ORGANISM: Artificial Sequence
<220> FEATURE:
<223> OTHER INFORMATION: Synthesized construct

<400> SEQUENCE: 9

```
Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Leu Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: Synthesized construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Leu Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 11
<211> LENGTH: 341
<212> TYPE: PRT
<213> ORGANISM: Artificial Sequence
<220> FEATURE:
<223> OTHER INFORMATION: Synthesized construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Leu Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg Val Glu Pro Lys
            100                 105                 110
```

```
Ser Ser Asp Lys Thr His Thr Cys Pro Pro Cys Pro Ala Pro Glu Leu
    115                 120                 125

Leu Gly Gly Pro Ser Val Phe Leu Phe Pro Pro Lys Pro Lys Asp Thr
130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Asp Glu Leu Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 12
<211> LENGTH: 16
<212> TYPE: PRT
<213> ORGANISM: Artificial Sequence
<220> FEATURE:
<223> OTHER INFORMATION: Synthesized construct
<220> FEATURE:
<221> NAME/KEY: VARIANT
<222> LOCATION: 5
<223> OTHER INFORMATION: In this sequence, the Cys which normally occurs
      at position 5 is replaced by the Ser residue.

<400> SEQUENCE: 12

Glu Pro Lys Ser Ser Asp Lys Thr His Thr Cys Pro Pro Cys Pro Ala
1               5                   10                  15

<210> SEQ ID NO 13
<211> LENGTH: 18
<212> TYPE: DNA
<213> ORGANISM: Artificial Sequence
<220> FEATURE:
<223> OTHER INFORMATION: Synthesized construct

<400> SEQUENCE: 13
aatckcaggt kccagatg                                                    18

<210> SEQ ID NO 14
<211> LENGTH: 18
```

```
<212> TYPE: DNA
<213> ORGANISM: Artificial Sequence
<220> FEATURE:
<223> OTHER INFORMATION: Synthesized construct

<400> SEQUENCE: 14
gttyrggtkk gtaacact                                                   18

<210> SEQ ID NO 15
<211> LENGTH: 18
<212> TYPE: DNA
<213> ORGANISM: Artificial Sequence
<220> FEATURE:
<223> OTHER INFORMATION: Synthesized construct

<400> SEQUENCE: 15
atgmcttgtw acactgtg                                                   18

<210> SEQ ID NO 16
<211> LENGTH: 267
<212> TYPE: DNA
<213> ORGANISM: Callithrix, species unknown

<400> SEQUENCE: 16
gacatccaga tgacccagtc tccatcttcc ctgactgcat ctgtaggagg caaagtcacc     60
atcacttgcc gggcgagtca ggacattaac aagtggttag cctggtatca gcagaaacca   120
gggacagtcc ctaagcccct gatctatgag gcatccaaat tgcaaagtgg ggtcccatca   180
aggttcagcg gcagtggatc tgggacatat tttactctca ccatcagcag cctgcagcct   240
gaagatgctg caacttatta ctgtcag                                        267

<210> SEQ ID NO 17
<211> LENGTH: 267
<212> TYPE: DNA
<213> ORGANISM: Callithrix, species unkwown

<400> SEQUENCE: 17
gacatccaga tgatccagtc tccatcctcc ctgtctgcat ctgtaggaga cagagtcacc     60
atcacttgct gggcaagtca gggtattagc cactggttag cctggtatca gcagaaacca   120
gggaaagccc ctaagctcct gatctatagt gcatcaaatt tagaaacagg ggtcccatca   180
aggttcagtg gaagtggatc caggacagat tttactctca ccatcagcag cctgcagcct   240
gaagatattg caacatatta ctgtcaa                                        267

<210> SEQ ID NO 18
<211> LENGTH: 267
<212> TYPE: DNA
<213> ORGANISM: Callithrix, species unkwown

<400> SEQUENCE: 18
gacatccaga tgacccagac tccatcctcc ctgtctgcat ctgtaggaga cagagtcacc     60
atcacttgcc gggcaagtca gggtattagc agctggttag cctggtatca gcagaaacca   120
gggaaagccc ctaagctcct gatctatggg gcatcaaatt tggaaacagg ggtcccatca   180
agattcagcg gaagtggatc tgggacagat tttactctca ccatcagcag tctgcagcct   240
gaagatattg caacatatta ctgtcaa                                        267

<210> SEQ ID NO 19
<211> LENGTH: 267
<212> TYPE: DNA
```

```
<213> ORGANISM: Callithrix, species unknown

<400> SEQUENCE: 19
gacatccaga tgatccagtc tccatcctcc ctgtctgcat ctgtaggaga cagagtcacc    60
atcacttgct gggcaagtca gggtattagc cactggttag cctggtatca gcagaaacca   120
gggaaagccc ctaagctcct gatctatagt gcatcaaatt taggaacagg ggtcccatca   180
aggttcagtg aagtggatc caggacagat tttactctca ccatcagcag cctgcagcct   240
gaagatattg caacatatta ctgtcaa                                       267

<210> SEQ ID NO 20
<211> LENGTH: 267
<212> TYPE: DNA
<213> ORGANISM: Callithrix, species unknown

<400> SEQUENCE: 20
gacatccaga tgacccagtc tccatcttcc ctgactgcat ctgtaggagg caaagtcacc    60
atcacttgcc gggcgtgtca ggacattaac aagtggttag cctggtatca gcagaaacca   120
gggacagtcc ctaagcccct gatctatgag gcatccaaat tgcaaagtgg ggtcccatca   180
aggttcagcg gcagtggatc tgggacatat tttactctca ccatcagcag cctgcagcct   240
gaagatgctg caacttatta ctgtcag                                       267

<210> SEQ ID NO 21
<211> LENGTH: 267
<212> TYPE: DNA
<213> ORGANISM: Caliithrix, species unknown

<400> SEQUENCE: 21
gacatccaga tgacccagtc tccatcctcc ctgtctgcat ctgtaggaga cagagttacc    60
atcacttgcc gggcgagtca gggcattagt aattatttag cctggtatca gcagaaacca   120
gggaaaactc ctaggctcct gatctatgct gcatccagtt tacaaactgg gattccctct   180
cggttcagcg gcagtggatc tgggacagac tacactctca ccatcagcag cctgcagtct   240
gaagatgttg caatttatta ctgtcaa                                       267

<210> SEQ ID NO 22
<211> LENGTH: 267
<212> TYPE: DNA
<213> ORGANISM: Callithrix, species unknown

<400> SEQUENCE: 22
gacatccaga tgacccagtc tccatcttcc ctgactgcat ctgtaggagg caaagtcacc    60
atcacttgcc gggcgagtca ggacattaac aagtggttag cctggtatca gcagaaacca   120
gggacagtcc ctaagcccct gatctatgag gcatccaaat tgcaaagtgg ggtcccatca   180
aggctcagcg gcagtggatc tgggacatat ttcactctca ccatcagcag cctgcagcct   240
gaagatgctg caacttatta ctgtcag                                       267

<210> SEQ ID NO 23
<211> LENGTH: 267
<212> TYPE: DNA
<213> ORGANISM: Callithrix, species unknown

<400> SEQUENCE: 23
gacatccaga tgacccagtc tccatcttcc ctgactgcat ctgtaggagg caaagtcacc    60
atcacttgcc gggcgagtca ggacattaac aagtggtcag cctggtatca gcagaaacca   120
```

```
gggacagtcc ctaagcccct gatctatgag gcatccaaat tgcaaagtgg ggtcccatca    180
aggttcagcg gcagtggatc tgggacatat tttactctca ccatcagcag cctgcagcct    240
gaagatgctg caacttatta ctgtcag                                        267
```

<210> SEQ ID NO 24
<211> LENGTH: 267
<212> TYPE: DNA
<213> ORGANISM: Callithrix, species unknown

<400> SEQUENCE: 24

```
gacatccaga tgacccagtc tccatcttcc ctgactgcat ctgtaggagg caaagtcacc     60
gtcacttgcc gggcgagtca ggacattaac aagtggttag cctggtatca gcagaaacca    120
gggacagtcc ctaagcccct gatctatgag gcatccaaat tgcaaagtgg ggtcccatca    180
aggttcagcg gcagtggatc tgggacatat tttactctca ccatcagcag cctgcagcct    240
gaagatgctg caacttatta ctgtcag                                        267
```

<210> SEQ ID NO 25
<211> LENGTH: 267
<212> TYPE: DNA
<213> ORGANISM: Callithrix, species unknown

<400> SEQUENCE: 25

```
gacatccaga tgacccagtc tccatcttcc ctgactgcat ctgtaggagg caaagtcacc     60
atcacttgcc gggcgagtca ggacattaac aagtggttag cctggtatca gcagaaacca    120
gggacagtcc ttaagcccct gatctatgag gcatccaaat tgcaaagtgg ggtcccatca    180
aggttcagcg gcagtggatc tgggacatat tttactctca ccatcagcag cctgcagcct    240
gaagatgctg caacttatta ctgtcag                                        267
```

<210> SEQ ID NO 26
<211> LENGTH: 267
<212> TYPE: DNA
<213> ORGANISM: Callithrix, species unknown

<400> SEQUENCE: 26

```
gacatccaga tgacccagtc tccatcttcc ctgactgcat ctgtaggagg caaagtcacc     60
atcacttgcc gggcgagtca ggacattaac aagtggttag cctggtatca gcagaaacca    120
gggacagtcc ctaagcccct gatctatgag gcatccaaat tgcaaagtgg ggtcccatta    180
aggttcagcg gcagtggatc tgggacatat tttactctca ccatcagcag cctgcagcct    240
gaagatgctg caacttatta ctgtcag                                        267
```

<210> SEQ ID NO 27
<211> LENGTH: 89
<212> TYPE: PRT
<213> ORGANISM: Callithrix, species unknown

<400> SEQUENCE: 27

```
Asp Ile Gln Met Thr Gln Ser Pro Ser Ser Leu Thr Ala Ser Val Gly
 1               5                  10                  15

Gly Lys Val Thr Ile Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
```

```
                50                  55                  60
Ser Gly Ser Gly Thr Tyr Phe Thr Leu Thr Ile Ser Ser Leu Gln Pro
 65                  70                  75                  80

Glu Asp Ala Ala Thr Tyr Tyr Cys Gln
                 85

<210> SEQ ID NO 28
<211> LENGTH: 89
<212> TYPE: PRT
<213> ORGANISM: Callithrix, species unknown

<400> SEQUENCE: 28

Asp Ile Gln Met Ile Gln Ser Pro Ser Ser Leu Ser Ala Ser Val Gly
 1               5                  10                  15

Asp Arg Val Thr Ile Thr Cys Trp Ala Ser Gln Gly Ile Ser His Trp
                20                  25                  30

Leu Ala Trp Tyr Gln Gln Lys Pro Gly Lys Ala Pro Lys Leu Leu Ile
             35                  40                  45

Tyr Ser Ala Ser Asn Leu Glu Thr Gly Val Pro Ser Arg Phe Ser Gly
 50                  55                  60

Ser Gly Ser Arg Thr Asp Phe Thr Leu Thr Ile Ser Ser Leu Gln Pro
 65                  70                  75                  80

Glu Asp Ile Ala Thr Tyr Tyr Cys Gln
                 85

<210> SEQ ID NO 29
<211> LENGTH: 89
<212> TYPE: PRT
<213> ORGANISM: Callithrix, species unknown

<400> SEQUENCE: 29

Asp Ile Gln Met Thr Gln Thr Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
             35                  40                  45

Tyr Gly Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln
                 85

<210> SEQ ID NO 30
<211> LENGTH: 89
<212> TYPE: PRT
<213> ORGANISM: Callithrix, species unknown

<400> SEQUENCE: 30

Asp Ile Gln Met Ile Gln Ser Pro Ser Ser Leu Ser Ala Ser Val Gly
 1               5                  10                  15

Asp Arg Val Thr Ile Thr Cys Trp Ala Ser Gln Gly Ile Ser His Trp
                20                  25                  30

Leu Ala Trp Tyr Gln Gln Lys Pro Gly Lys Ala Pro Lys Leu Leu Ile
             35                  40                  45

Tyr Ser Ala Ser Asn Leu Gly Thr Gly Val Pro Ser Arg Phe Ser Gly
 50                  55                  60
```

```
Ser Gly Ser Arg Thr Asp Phe Thr Leu Thr Ile Ser Ser Leu Gln Pro
65                  70                  75                  80

Glu Asp Ile Ala Thr Tyr Tyr Cys Gln
                85

<210> SEQ ID NO 31
<211> LENGTH: 89
<212> TYPE: PRT
<213> ORGANISM: Callithrix, species unknown

<400> SEQUENCE: 31

Asp Ile Gln Met Thr Gln Ser Pro Ser Ser Leu Thr Ala Ser Val Gly
1               5                   10                  15

Gly Lys Val Thr Ile Thr Cys Arg Ala Cys Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 32
<211> LENGTH: 89
<212> TYPE: PRT
<213> ORGANISM: Callithrix, species unknown

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Thr Pro Arg Leu Leu Ile
        35                  40                  45

Tyr Ala Ala Ser Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Ser
65                  70                  75                  80

Glu Asp Val Ala Ile Tyr Tyr Cys Gln
                85

<210> SEQ ID NO 33
<211> LENGTH: 89
<212> TYPE: PRT
<213> ORGANISM: Callithrix, species unknown

<400> SEQUENCE: 33

Asp Ile Gln Met Thr Gln Ser Pro Ser Ser Leu Thr Ala Ser Val Gly
1               5                   10                  15

Gly Lys Val Thr Ile Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Leu Ser Gly
    50                  55                  60
```

```
Ser Gly Ser Gly Thr Tyr Phe Thr Leu Thr Ile Ser Ser Leu Gln Pro
 65                  70                  75                  80

Glu Asp Ala Ala Thr Tyr Tyr Cys Gln
                 85

<210> SEQ ID NO 34
<211> LENGTH: 89
<212> TYPE: PRT
<213> ORGANISM: Callithrix, species unknown

<400> SEQUENCE: 34

Asp Ile Gln Met Thr Gln Ser Pro Ser Ser Leu Thr Ala Ser Val Gly
 1               5                  10                  15

Gly Lys Val Thr Ile Thr Cys Arg Ala Ser Gln Asp Ile Asn Lys Trp
                 20                  25                  30

Ser Ala Trp Tyr Gln Gln Lys Pro Gly Thr Val Pro Lys Pro Leu Ile
             35                  40                  45

Tyr Glu Ala Ser Lys Leu Gln Ser Gly Val Pro Ser Arg Phe Ser Gly
 50                  55                  60

Ser Gly Ser Gly Thr Tyr Phe Thr Leu Thr Ile Ser Ser Leu Gln Pro
 65                  70                  75                  80

Glu Asp Ala Ala Thr Tyr Tyr Cys Gln
                 85

<210> SEQ ID NO 35
<211> LENGTH: 89
<212> TYPE: PRT
<213> ORGANISM: Callithrix, species unknown

<400> SEQUENCE: 35

Asp Ile Gln Met Thr Gln Ser Pro Ser Ser Leu Thr Ala Ser Val Gly
 1               5                  10                  15

Gly Lys Val Thr Val Thr Cys Arg Ala Ser Gln Asp Ile Asn Lys Trp
                 20                  25                  30

Leu Ala Trp Tyr Gln Gln Lys Pro Gly Thr Val Pro Lys Pro Leu Ile
             35                  40                  45

Tyr Glu Ala Ser Lys Leu Gln Ser Gly Val Pro Ser Arg Phe Ser Gly
 50                  55                  60

Ser Gly Ser Gly Thr Tyr Phe Thr Leu Thr Ile Ser Ser Leu Gln Pro
 65                  70                  75                  80

Glu Asp Ala Ala Thr Tyr Tyr Cys Gln
                 85

<210> SEQ ID NO 36
<211> LENGTH: 89
<212> TYPE: PRT
<213> ORGANISM: Callithrix, species unknown

<400> SEQUENCE: 36

Asp Ile Gln Met Thr Gln Ser Pro Ser Ser Leu Thr Ala Ser Val Gly
 1               5                  10                  15

Gly Lys Val Thr Ile Thr Cys Arg Ala Ser Gln Asp Ile Asn Lys Trp
                 20                  25                  30

Leu Ala Trp Tyr Gln Gln Lys Pro Gly Thr Val Leu Lys Pro Leu Ile
             35                  40                  45

Tyr Glu Ala Ser Lys Leu Gln Ser Gly Val Pro Ser Arg Phe Ser Gly
 50                  55                  60

Ser Gly Ser Gly Thr Tyr Phe Thr Leu Thr Ile Ser Ser Leu Gln Pro
```

Glu Asp Ala Ala Thr Tyr Tyr Cys Gln
                    85

<210> SEQ ID NO 37
<211> LENGTH: 89
<212> TYPE: PRT
<213> ORGANISM: Callithrix, species unkwown

<400> SEQUENCE: 37

Asp Ile Gln Met Thr Gln Ser Pro Ser Ser Leu Thr Ala Ser Val Gly
1               5                   10                  15

Gly Lys Val Thr Ile Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Leu Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                    85

<210> SEQ ID NO 38
<211> LENGTH: 267
<212> TYPE: DNA
<213> ORGANISM: Aotus trivirgatus

<400> SEQUENCE: 38
gacatccaga tgacccagtc tccatccttc ctgtctgcat ctgcaggaga cagagtcacc      60
atcacctgcc aggtgagtca gggaattagc agtgaattac tctggtatca gcagaaacca     120
gggaaagccc ctatgctctt gatctatgct gcaaccaaat tgcagtcggg aatcccatct     180
cggttcagtg gcatggatc tgggacagat ttcactctca ccatcagcag cctgcagcct     240
gatgattttg ctacttatta ctgtcaa                                         267

<210> SEQ ID NO 39
<211> LENGTH: 267
<212> TYPE: DNA
<213> ORGANISM: Aotus trivirgatus

<400> SEQUENCE: 39
gacatccaga tgacccagtc tgcattctcc ctgtctgcat ctgtaggaga cagagtcacc      60
attacttgcc aggcgagtca gggcattacc agtgatttag cctggtatca gcaaaagcca     120
gggaacgcct ctaagctcct gatctatgag gcatccagtt tacaaagcga ggtcccatca     180
aggttcagcg gcagtggatc tgggagagat tttactctca ccatcagcag cctgcagcct     240
gaagattttg taacttatta ctgtcaa                                         267

<210> SEQ ID NO 40
<211> LENGTH: 267
<212> TYPE: DNA
<213> ORGANISM: Aotus trivirgatus

<400> SEQUENCE: 40
gacatccaga tgacccagac tccatcctcc ctgtctgcat ctgtaggaga cagagtcacc      60
atcacttgcc gggcgagtca agacatttac aattatttag cctggtatca gcagaaacca    120

```
gggaaaactc ctaggctctt gatctatgct gcatccagtt tgcaaactgg gattccctct    180
cggttcagtg gcagtggatc tgggacagac tacactctca ccatcagcag cctgcagcct    240
gatgattttg ccacttatta ctgtcaa                                        267
```

<210> SEQ ID NO 41
<211> LENGTH: 267
<212> TYPE: DNA
<213> ORGANISM: Aotus trivirgatus

<400> SEQUENCE: 41

```
gacatccaga tgacccagac tccatcctcc ctgcctgcat ctgtaggaga caaagtcacc    60
atcacttgcc gggcaagtca gggtattagc agctggttag cctggtatca gcagaaacca    120
gggaaagccc ctaagctcct gatccataag gcatcaaatt tggaaacagg gtcccatca    180 aggttcagtg gaagtggatc tgggacagat tttactctca ccatcagcag cctgcagcct    240
gaagatatcg caacatatta ctgtcaa                                        267
```

<210> SEQ ID NO 42
<211> LENGTH: 267
<212> TYPE: DNA
<213> ORGANISM: Aotus trivirgatus

<400> SEQUENCE: 42

```
gacatccaga tgacccagtc tccatcttcc ctgactgcat ctgtaggaga caaagtcacc    60
atcacttgcc gggcaagtca gggcattagc aataatttag cctggtatca gcagaaacca    120
gggaaagccc ctaagcccct gatctattat gcatccagtt tgcaaagcgg ggtcccatca    180
aggttcagcg gcagtggatc tggggcagat tacactctca ccaccagcag cctgcagcct    240
gaagattttg caacttatta ctgtcaa                                        267
```

<210> SEQ ID NO 43
<211> LENGTH: 267
<212> TYPE: DNA
<213> ORGANISM: Aotus trivirgatus

<400> SEQUENCE: 43

```
gacaaccaga tgatccagtc tccatcttcc ctgactgcat ctgtaggaga cagagtcacc    60
atcacttgcc gagccagtca gagtattagc agctggttag cctggtatca gcagaaacca    120
gggacagtcc ctaagcctct gatctatgac gcatccaaat tgctaagtgg ggtcccatca    180
aggttcagtg gctgtggatc tgggacagat tttactctca ccatcagcag cctgcagcct    240
gaagattttg caacttatta ctgtcaa                                        267
```

<210> SEQ ID NO 44
<211> LENGTH: 89
<212> TYPE: PRT
<213> ORGANISM: Aotus trivirgatus

<400> SEQUENCE: 44

Asp Ile Gln Met Thr Gln Ser Pro Ser Phe Leu Ser Ala Ser Ala Gly
 1               5                  10                  15

Asp Arg Val Thr Ile Thr Cys Gln Val Ser Gln Gly Ile Ser Ser Glu
             20                  25                  30

Leu Leu Trp Tyr Gln Gln Lys Pro Gly Lys Ala Pro Met Leu Leu Ile
         35                  40                  45

Tyr Ala Ala Thr Lys Leu Gln Ser Gly Ile Pro Ser Arg Phe Ser Gly
     50                  55                  60

His Gly Ser Gly Thr Asp Phe Thr Leu Thr Ile Ser Ser Leu Gln Pro
65                  70                  75                  80

Asp Asp Phe Ala Thr Tyr Tyr Cys Gln
                85

<210> SEQ ID NO 45
<211> LENGTH: 89
<212> TYPE: PRT
<213> ORGANISM: Aotus trivirgatus

<400> SEQUENCE: 45

Asp Ile Gln Met Thr Gln Ser Ala Phe Ser Leu Ser Ala Ser Val Gly
1               5                   10                  15

Asp Arg Val Thr Ile Thr Cys Gln Ala Ser Gln Gly Ile Thr Ser Asp
                20                  25                  30

Leu Ala Trp Tyr Gln Gln Lys Pro Gly Asn Ala Ser Lys Leu Leu Ile
            35                  40                  45

Tyr Glu Ala Ser Ser Leu Gln Ser Glu Val Pro Ser Arg Phe Ser Gly
        50                  55                  60

Ser Gly Ser Gly Arg Asp Phe Thr Leu Thr Ile Ser Ser Leu Gln Pro
65                  70                  75                  80

Glu Asp Phe Val Thr Tyr Tyr Cys Gln
                85

<210> SEQ ID NO 46
<211> LENGTH: 89
<212> TYPE: PRT
<213> ORGANISM: Aotus trivirgatus

<400> SEQUENCE: 46

Asp Ile Gln Met Thr Gln Thr Pro Ser Ser Leu Ser Ala Ser Val Gly
1               5                   10                  15

Asp Arg Val Thr Ile Thr Cys Arg Ala Ser Gln Asp Ile Tyr Asn Tyr
                20                  25                  30

Leu Ala Trp Tyr Gln Gln Lys Pro Gly Lys Thr Pro Arg Leu Leu Ile
            35                  40                  45

Tyr Ala Ala Ser Ser Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Asp Asp Phe Ala Thr Tyr Tyr Cys Gln
                85

<210> SEQ ID NO 47
<211> LENGTH: 89
<212> TYPE: PRT
<213> ORGANISM: Aotus trivirgatus

<400> SEQUENCE: 47

Asp Ile Gln Met Thr Gln Thr Pro Ser Ser Leu Pro Ala Ser Val Gly
1               5                   10                  15

Asp Lys Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

His Lys Ala Ser Asn Leu Glu Thr Gly Val Pro Ser Arg Phe Ser Gly
        50                  55                  60

```
Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln
                 85

<210> SEQ ID NO 48
<211> LENGTH: 89
<212> TYPE: PRT
<213> ORGANISM: Aotus trivirgatus

<400> SEQUENCE: 48

Asp Ile Gln Met Thr Gln Ser Pro Ser Ser Leu Thr Ala Ser Val Gly
  1               5                  10                  15

Asp Lys Val Thr Ile Thr Cys Arg Ala Ser Gln Gly Ile Ser Asn Asn
                 20                  25                  30

Leu Ala Trp Tyr Gln Gln Lys Pro Gly Lys Ala Pro Lys Pro Leu Ile
             35                  40                  45

Tyr Tyr Ala Ser Ser Leu Gln Ser Gly Val Pro Ser Arg Phe Ser Gly
         50                  55                  60

Ser Gly Ser Gly Ala Asp Tyr Thr Leu Thr Thr Ser Ser Leu Gln Pro
 65                  70                  75                  80

Glu Asp Phe Ala Thr Tyr Tyr Cys Gln
                 85

<210> SEQ ID NO 49
<211> LENGTH: 89
<212> TYPE: PRT
<213> ORGANISM: Aotus trivirgatus

<400> SEQUENCE: 49

Asp Asn Gln Met Ile Gln Ser Pro Ser Ser Leu Thr Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Thr Val Pro Lys Pro Leu Ile
             35                  40                  45

Tyr Asp Ala Ser Lys Leu Leu Ser Gly Val Pro Ser Arg Phe Ser Gly
         50                  55                  60

Cys Gly Ser Gly Thr Asp Phe Thr Leu Thr Ile Ser Ser Leu Gln Pro
 65                  70                  75                  80

Glu Asp Phe Ala Thr Tyr Tyr Cys Gln
                 85

<210> SEQ ID NO 50
<211> LENGTH: 1023
<212> TYPE: DNA
<213> ORGANISM: Artificial Sequence
<220> FEATURE:
<223> OTHER INFORMATION: Synthesized construct

<400> SEQUENCE: 50
gacatccaga tgacccagag ccccagcagc ctgagcgcct ctgtgggcga tagagtgacc      60
atcacctgca gagccagcca ggccatcgac agctacctgc actggtatca gcagaagcct     120
ggcaaggccc ctaagctgct gatctacagc gccagcaatc tggagaccgg cgtgcctagc     180
agattcagcg gcagcggctc cggcaccgac ttcaccctga ccatcagcag cctgctgcct     240
gaggatttcg ccacctacta ctgccagcag gtggtgtgga gacctttcac cttcggccag     300
ggcaccaagg tggagatcaa gcgggtggag cccaagagct gcgataagac ccacacctgc     360
```

```
cccccctgcc ctgcccccga gctgctgggc ggacccagcg tgttcctgtt ccccccaag      420 cctaaggaca ccctgatgat cagcagaacc cccgaggtga cctgcgtggt ggtggatgtg     480
agccacgagg accctgaggt gaagttcaac tggtacgtgg acggcgtgga ggtgcacaat     540
gccaagacca agcccaggga ggagcagtac aacagcacct accgggtggt gtccgtgctg     600
accgtgctgc accaggattg gctgaacggc aaggagtaca agtgcaaggt gtccaacaag     660
gccctgcctg cccctatcga aaaaccatc agcaaggcca agggccagcc cagagagccc      720
caggtgtaca ccctgccccc tagcagagat gagctgacca gaaccaggt gtccctgacc      780 tgcctggtga agggcttcta ccccagcgac atcgccgtgg agtgggagag caacggccag     840
cccgagaaca actacaagac cacccccct gtgctggaca cgatggcag cttcttcctg       900 tacagcaagc tgaccgtgga caagagcaga tggcagcagg gcaacgtgtt cagctgcagc     960
gtgatgcacg aggccctgca caatcactac acccagaaga gcctgagcct gtcccctggc    1020
aag                                                                  1023

<210> SEQ ID NO 51
<211> LENGTH: 1023
<212> TYPE: DNA
<213> ORGANISM: Artificial Sequence
<220> FEATURE:
<223> OTHER INFORMATION: Synthesized construct

<400> SEQUENCE: 51
gacatccaga tgacccagag ccccagcagc ctgagcgcct ctgtgggcga tagagtgacc       60
atcacctgca gagccagcca ggccatcgac agctacctgc actggtatca gcagaagcct     120
ggcaaggccc ctaagctgct gatctacagc gccagcaatc tggagaccgg cgtgcctagc     180
agattcagcg gcagcggctc cggcaccgac ttcaccctga ccatcagcag cctgctgcct     240
gaggatttcg ccacctacta ctgccagcag gtggtgtgga gaccttcac cttcggccag      300 ggcaccaagg tggagatcaa gcgggtggag cccaagagca gcgataagac ccacacctgc     360
cccccctgcc ctgcccccga gctgctgggc ggacccagcg tgttcctgtt ccccccaag     420 cctaaggaca ccctgatgat cagcagaacc cccgaggtga cctgcgtggt ggtggatgtg    480
agccacgagg accctgaggt gaagttcaac tggtacgtgg acggcgtgga ggtgcacaat    540
gccaagacca agcccaggga ggagcagtac aacagcacct accgggtggt gtccgtgctg    600
accgtgctgc accaggattg gctgaacggc aaggagtaca agtgcaaggt gtccaacaag    660
gccctgcctg cccctatcga aaaaccatc agcaaggcca agggccagcc cagagagccc     720
caggtgtaca ccctgccccc tagcagagat gagctgacca gaaccaggt gtccctgacc     780 tgcctggtga agggcttcta ccccagcgac atcgccgtgg agtgggagag caacggccag    840
cccgagaaca actacaagac cacccccct gtgctggaca cgatggcag cttcttcctg      900 tacagcaagc tgaccgtgga caagagcaga tggcagcagg gcaacgtgtt cagctgcagc    960
gtgatgcacg aggccctgca caatcactac acccagaaga gcctgagcct gtcccctggc   1020
aag                                                                 1023

<210> SEQ ID NO 52
<211> LENGTH: 108
<212> TYPE: PRT
<213> ORGANISM: Artificial Sequence
<220> FEATURE:
<223> OTHER INFORMATION: Synthesized construct
```

```
<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

```
<210> SEQ ID NO 53
<211> LENGTH: 108
<212> TYPE: PRT
<213> ORGANISM: Artificial Sequence
<220> FEATURE:
<223> OTHER INFORMATION: Synthesized construct

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

```
<210> SEQ ID NO 54
<211> LENGTH: 108
<212> TYPE: PRT
<213> ORGANISM: Artificial Sequence
<220> FEATURE:
<223> OTHER INFORMATION: Synthesized construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Val Pro
65                  70                  75                  80
```

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 55
<211> LENGTH: 8
<212> TYPE: PRT
<213> ORGANISM: Artificial Sequence
<220> FEATURE:
<223> OTHER INFORMATION: Synthesized construct

<400> SEQUENCE: 55

Tyr Ser Ala Ser Glu Leu Gln Ser
1               5

<210> SEQ ID NO 56
<211> LENGTH: 8
<212> TYPE: PRT
<213> ORGANISM: Aotus trivirgatus

<400> SEQUENCE: 56

Tyr Tyr Ala Ser Ser Leu Gln Ser
1               5

<210> SEQ ID NO 57
<211> LENGTH: 6
<212> TYPE: PRT
<213> ORGANISM: Artificial Sequence
<220> FEATURE:
<223> OTHER INFORMATION: Synthesized construct

<400> SEQUENCE: 57

Gly Cys Cys Ala Cys Cys
1               5

<210> SEQ ID NO 58
<211> LENGTH: 20
<212> TYPE: PRT
<213> ORGANISM: Artificial Sequence
<220> FEATURE:
<223> OTHER INFORMATION: Synthesized construct

<400> SEQUENCE: 58

Met Ser Val Pro Thr Gln Val Leu Gly Leu Leu Leu Leu Trp Leu Thr
1               5                   10                  15

Asp Ala Arg Cys
            20

<210> SEQ ID NO 59
<211> LENGTH: 341
<212> TYPE: PRT
<213> ORGANISM: Artificial Sequence
<220> FEATURE:
<223> OTHER INFORMATION: Synthesized construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly

```
                     50                  55                  60
Ser Gly Ser Gly Thr Asp Phe Thr Leu Thr Ile Ser Ser Leu Leu Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg Val Glu Pro Lys
            100                 105                 110

Ser Cys Asp Lys Thr His Thr Cys Pro Pro Cys Pro Ala Pro Glu Leu
            115                 120                 125

Leu Gly Gly Pro Ser Val Phe Leu Phe Pro Pro Lys Pro Lys Asp Thr
130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Asp Glu Leu Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 60
<211> LENGTH: 329
<212> TYPE: PRT
<213> ORGANISM: Artificial Sequence
<220> FEATURE:
<223> OTHER INFORMATION: Synthesized construct

<400> SEQUENCE: 60

Ser Thr Lys Gly Pro Ser Val Phe Pro Leu Ala Pro Ser Ser Lys Ser
 1               5                  10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
```

```
                65                  70                  75                  80
        Ile Cys Asn Val Asn His Lys Pro Ser Asn Thr Lys Val Asp Lys Arg
                        85                  90                  95

Val Glu Pro Lys Ser Cys Asp Lys Thr His Thr Cys Pro Pro Cys Pro
                        100                 105                 110

Ala Pro Glu Leu Leu Gly Gly Pro Ser Val Phe Leu Phe Pro Pro Lys
                        115                 120                 125

Pro Lys Asp Thr Leu Met Ile Ser Arg Thr Pro Glu Val Thr Cys Val
                    130                 135                 140

Val Val Asp Val Ser His Glu Asp Pro Glu Val Lys Phe Asn Trp Tyr
        145                 150                 155                 160

Val Asp Gly Val Glu Val His Asn Ala Lys Thr Lys Pro Arg Glu Glu
                        165                 170                 175

Gln Tyr Asn Ser Thr Tyr Arg Val Val Ser Val Leu Thr Val Leu His
                        180                 185                 190

Gln Asp Trp Leu Asn Gly Lys Glu Tyr Lys Cys Lys Val Ser Asn Lys
                        195                 200                 205

Ala Leu Pro Ala Pro Ile Glu Lys Thr Ile Ser Lys Ala Lys Gly Gln
                    210                 215                 220

Pro Arg Glu Pro Gln Val Tyr Thr Leu Pro Pro Ser Arg Glu Glu Met
        225                 230                 235                 240

Thr Lys Asn Gln Val Ser Leu Thr Cys Leu Val Lys Gly Phe Tyr Pro
                        245                 250                 255

Ser Asp Ile Ala Val Glu Trp Glu Ser Asn Gly Gln Pro Glu Asn Asn
                        260                 265                 270

Tyr Lys Thr Thr Pro Pro Val Leu Asp Ser Asp Gly Ser Phe Phe Leu
                    275                 280                 285

Tyr Ser Lys Leu Thr Val Asp Lys Ser Arg Trp Gln Gln Gly Asn Val
                    290                 295                 300

Phe Ser Cys Ser Val Met His Glu Ala Leu His Asn His Tyr Thr Gln
        305                 310                 315                 320

Lys Ser Leu Ser Leu Ser Pro Gly Lys
                        325

<210> SEQ ID NO 61
<211> LENGTH: 1044
<212> TYPE: DNA
<213> ORGANISM: Artificial Sequence
<220> FEATURE:
<223> OTHER INFORMATION: Synthesized construct

<400> SEQUENCE: 61
atggcgagca ccgatattca gatgacccag agcccgagca gcctgagcgc gagcgtgggt      60
gatcgtgtga ccattacctg ccgtgcgagc caggcgattg atagctatct gcattggtat     120
cagcagaaac cgggcaaagc gccgaaactg ctgatttata cgcgcagcaa cctggaaacc     180
ggcgtgccga ccgttttagc ggcagcggt agcggcaccg attttaccct gaccattagc     240
agcctgctgc cggaagattt tgcgacctat tattgccagc aggtggtgtg cgtccgttt      300 acctttggcc agggcaccaa agtggaaatt aaacgcgtgg aaccgaaaag cagcgataaa     360
acccacacgt gcccgccgtg tccggcgccg aactgctgg gtggcccgag cgtgtttctg      420
tttccgccga aaccgaaaga taccctgatg attagccgta ccccggaagt gacctgcgtg     480
gtggtggatg tgagccatga agatccggaa gtgaaattca ctggtatgt ggatggcgtg      540 gaagtgcata acgcgaaaac caaaccgcgt gaagaacagt ataacagcac ctatcgtgtg     600
```

```
gtgagcgtgc tgaccgtgct gcatcaggat tggctgaacg gcaaagaata caaatgcaaa    660
gtgtctaaca aagcgctgcc ggcgccgatt gaaaaaacca tcagcaaagc gaaaggccag    720
ccgcgtgaac cgcaggtgta taccctgccg ccgagccgtg atgaactgac caaaaaccag    780
gtgagcctga cctgcctggt gaaaggcttt tatccgagcg atattgcggt ggaatgggaa    840
agcaacggcc agccggaaaa caactataaa accaccccgc cggtgctgga tagcgatggc    900
agctttttcc tgtatagcaa actgaccgtg gataaaagcc gttggcagca gggcaacgtg    960
tttagctgca gcgtgatgca tgaagcgctg cataaccatt atacccagaa aagcctgagc   1020
ctgagcccgg gtaaagcggc ggcg                                         1044
```

<210> SEQ ID NO 62
<211> LENGTH: 356
<212> TYPE: PRT
<213> ORGANISM: Artificial Sequence
<220> FEATURE:
<223> OTHER INFORMATION: Synthesized construct

<400> SEQUENCE: 62

```
Met Ala Ser Thr Asp Ile Gln Met Thr Gln Ser Pro Ser Ser Leu Ser
 1               5                   10                  15

Ala Ser Val Gly Asp Arg Val Thr Ile Thr Cys Arg Ala Ser Gln Ala
            20                  25                  30

Ile Asp Ser Tyr Leu His Trp Tyr Gln Gln Lys Pro Gly Lys Ala Pro
        35                  40                  45

Lys Leu Leu Ile Tyr Ser Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Leu Pro Glu Asp Phe Ala Thr Tyr Tyr Cys Gln Gln Val Val
                85                  90                  95

Trp Arg Pro Phe Thr Phe Gly Gln Gly Thr Lys Val Glu Ile Lys Arg
            100                 105                 110

Val Glu Pro Lys Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
```

```
                275                 280                 285
Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys Ala Ala Ala Val Asp His His
            340                 345                 350

His His His His
        355

<210> SEQ ID NO 63
<211> LENGTH: 216
<212> TYPE: PRT
<213> ORGANISM: CH2/CH3 domain sequence from Swissprot INSERT

<400> SEQUENCE: 63

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 64
<211> LENGTH: 17
<212> TYPE: PRT
<213> ORGANISM: Artificial Sequence
<220> FEATURE:
<223> OTHER INFORMATION: Synthesized construct
<220> FEATURE:
<221> NAME/KEY: VARIANT
<222> LOCATION: 1
<223> OTHER INFORMATION: Xaa = X is valine, leucine or isoleucine. It is
      preferred that X is valine.
```

```
<220> FEATURE:
<221> NAME/KEY: VARIANT
<222> LOCATION: 6
<223> OTHER INFORMATION: Xaa = X is absent or an amino acid other than
      cysteine. It is preferred by X is serine.

<400> SEQUENCE: 64

Xaa Glu Pro Lys Ser Xaa Asp Lys Thr His Thr Cys Pro Pro Cys Pro
 1               5                  10                  15

Ala

<210> SEQ ID NO 65
<211> LENGTH: 12
<212> TYPE: PRT
<213> ORGANISM: Artificial Sequence
<220> FEATURE:
<223> OTHER INFORMATION: Synthesized construct

<400> SEQUENCE: 65

Thr Lys Val Glu Ile Lys Arg Val Glu Pro Lys Ser
 1               5                  10

<210> SEQ ID NO 66
<211> LENGTH: 11
<212> TYPE: PRT
<213> ORGANISM: Homo Sapiens

<400> SEQUENCE: 66

Thr Lys Val Asp Lys Arg Val Glu Pro Lys Ser
 1               5                  10

<210> SEQ ID NO 67
<211> LENGTH: 11
<212> TYPE: PRT
<213> ORGANISM: Artificial Sequence
<220> FEATURE:
<223> OTHER INFORMATION: Synthesized construct

<400> SEQUENCE: 67

Thr Lys Val Glu Ile Lys Arg Glu Pro Lys Ser
 1               5                  10

<210> SEQ ID NO 68
<211> LENGTH: 324
<212> TYPE: DNA
<213> ORGANISM: Artificial Sequence
<220> FEATURE:
<223> OTHER INFORMATION: Synthesized construct

<400> SEQUENCE: 68
ctgtaggtct actgggtcag aggtaggaga gacagacgta gacatcctct ggcacagtgg      60
tagtgaacgg cccgttcagt ctcgtaacta tcaataaatg taaccatggt cgtctttggt     120
cccttcgggg gattcgagga ctagatatca cgtaggctca acgtttcacc ccagggtagt     180
gcaaagtcac cgtcacctag accctgtcta aagtgagagt ggtagtcgtc agacgttgga     240
cttctaaaac gatgcatgat gacagttgtc caacacaccg caggaaaatg caagccggtt     300
ccctggttcc acctttagtt tgcc                                            324
```